United States Patent
Yumikake et al.

(10) Patent No.: US 8,192,024 B2
(45) Date of Patent: Jun. 5, 2012

(54) OPTICAL IMAGE MEASUREMENT DEVICE AND PROGRAM FOR CONTROLLING THE SAME

(75) Inventors: Kazuhiko Yumikake, Nerima-ku (JP); Yutaka Nishio, Fussa (JP); Hiroaki Okada, Saitama (JP); Tsutomu Kikawa, Adachi-ku (JP)

(73) Assignee: Kabushiki Kaisha Topcon, Tokyo (JP)

(*) Notice: Subject to any disclaimer, the term of this patent is extended or adjusted under 35 U.S.C. 154(b) by 0 days.

(21) Appl. No.: 12/450,879

(22) PCT Filed: Apr. 8, 2008

(86) PCT No.: PCT/JP2008/000902
§ 371 (c)(1),
(2), (4) Date: Oct. 16, 2009

(87) PCT Pub. No.: WO2008/129863
PCT Pub. Date: Oct. 30, 2008

(65) Prior Publication Data
US 2010/0039616 A1 Feb. 18, 2010

(30) Foreign Application Priority Data

Apr. 18, 2007 (JP) ................................. 2007-109029

(51) Int. Cl.
*A61B 3/14* (2006.01)
*A61B 3/00* (2006.01)
*A61B 3/10* (2006.01)
(52) U.S. Cl. ......... 351/206; 351/200; 351/210; 351/221
(58) Field of Classification Search .................. 351/200, 351/205–206, 210, 221, 246
See application file for complete search history.

(56) References Cited

U.S. PATENT DOCUMENTS

| | | | | |
|---|---|---|---|---|
| 5,726,754 A | * | 3/1998 | Andrews et al. | 356/511 |
| 5,847,827 A | * | 12/1998 | Fercher | 356/493 |
| 2002/0051512 A1 | * | 5/2002 | Toida | 378/21 |
| 2007/0070295 A1 | | 3/2007 | Tsukada et al. | |

(Continued)

FOREIGN PATENT DOCUMENTS

EP 1 775 545 A2 4/2007

(Continued)

OTHER PUBLICATIONS

International Search Report dated May 13, 2008 issued in PCT/JP2008/000902.

*Primary Examiner* — Dawayne A Pinkney
(74) *Attorney, Agent, or Firm* — Edwards Wildman Palmer LLP

(57) ABSTRACT

A fundus oculi observation device 1 divides a low-coherence light L0 into a signal light LS and a reference light LR, superimposes the signal light LS propagated through a a fundus oculi Ef and the reference light LR propagated through a reference mirror 174 to generate and detect an interference light LC, and forms an OCT image of the fundus oculi Ef based on the result of the detection. The fundus oculi observation device 1 scans with the signal light LS while changing a scan interval when performing a series of scans with the signal light LS. Thus, it is possible to acquire a highly accurate image at small scan intervals from an attention site, and it is possible to reduce a scanning time by scanning at large intervals in other sites. Accordingly, it is possible to rapidly acquire a highly accurate image of an attention site.

19 Claims, 13 Drawing Sheets

U.S. PATENT DOCUMENTS

2007/0216909 A1 * 9/2007 Everett et al. ................. 356/479

FOREIGN PATENT DOCUMENTS

| | | |
|---|---|---|
| EP | 1962083 A1 * | 8/2008 |
| JP | 11-325849 | 11/1999 |
| JP | 2001-275979 | 10/2001 |
| JP | 2002-139421 | 5/2002 |
| JP | 2002-143088 | 5/2002 |
| JP | 2003-000543 | 1/2003 |
| JP | 2006-023476 | 1/2006 |

* cited by examiner

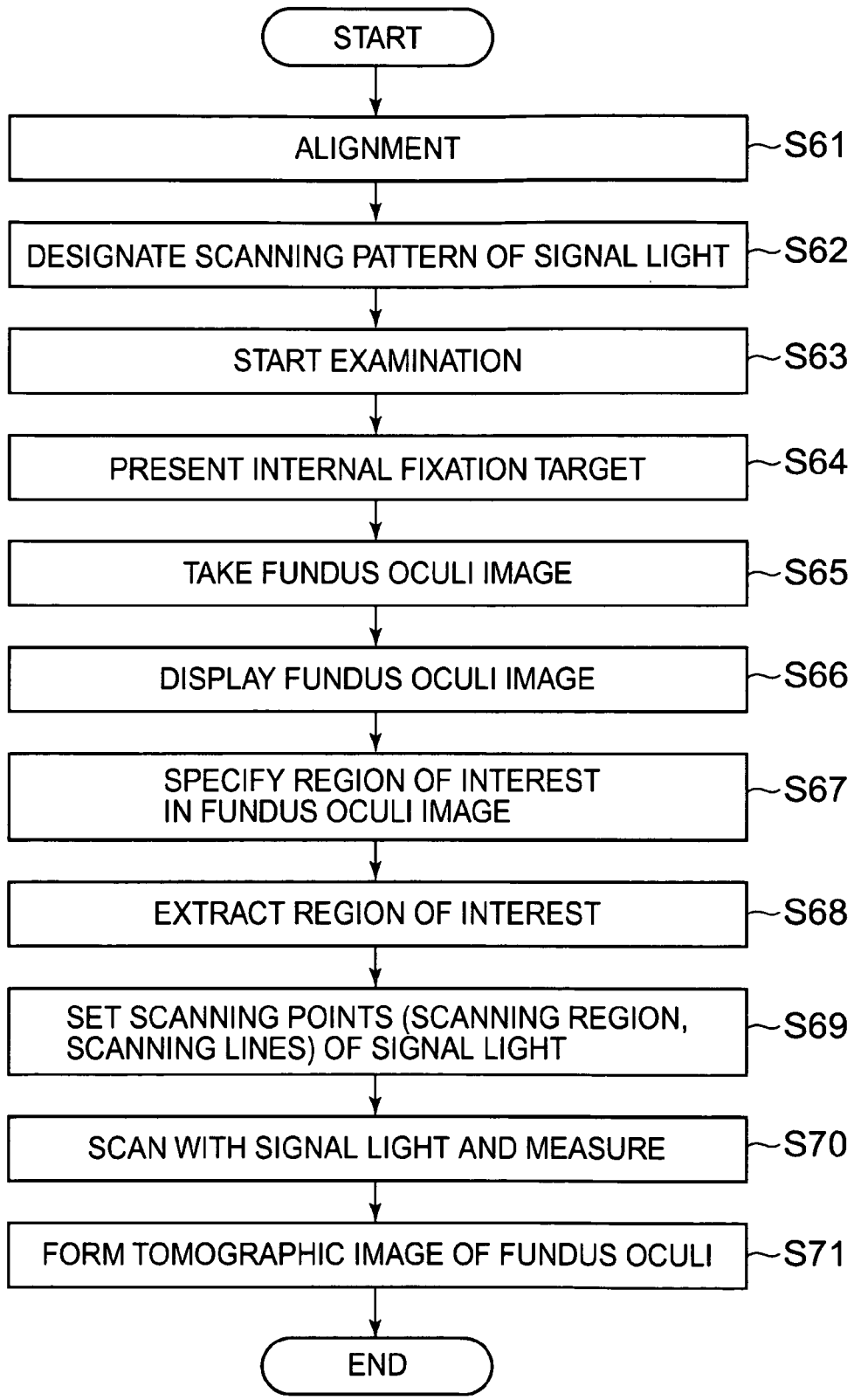

OPTICAL IMAGE MEASUREMENT DEVICE AND PROGRAM FOR CONTROLLING THE SAME

TECHNICAL FIELD

The present invention relates to an optical image measurement device that scans a measurement object with a light beam and forms an image of the measurement object by using the reflected light, and also relates to a program for controlling the optical image measurement device.

BACKGROUND ART

In recent years, attention has been focused on an optical image measurement technique of forming an image showing the surface morphology or internal morphology of a measurement object by using a light beam emitted from a laser light source or the like. Because this optical image measurement technique does not have invasiveness to human bodies unlike an X-ray CT device, it is expected to employ this technique particularly in the medical field.

Patent Document 1 discloses an optical image measurement device configured in a manner that: a measuring arm scans an object by using a rotary deflection mirror (Galvano mirror); a reference mirror is disposed to a reference arm; at the outlet thereof, such an interferometer is used that the intensity of a light caused by interference of light fluxes from the measuring arm and the reference arm is analyzed by a spectrometer; and the reference arm is provided with a device gradually changing the light flux phase of the reference light in non-continuous values.

The optical image measurement device disclosed in Patent Document 1 uses a method of so-called "Fourier Domain OCT (Optical Coherence Tomography)." That is to say, the morphology of the measurement object in the depth direction (z-direction) is imaged by applying a beam of a low-coherence light to a measurement object, obtaining the spectrum intensity distribution of the reflected light, and subjecting the obtained distribution to Fourier transform.

Furthermore, the optical image measurement device described in Patent Document 1 is provided with a Galvano mirror scanning with a light beam (a signal light), thereby being capable of forming an image of a desired measurement region of a measurement object.

Because this optical image measurement device scans with the light beam only in one direction (x-direction) orthogonal to the z-direction, a formed image is a 2-dimensional tomographic image in the depth direction (z-direction) along the scanning direction of the light beam (the x-direction).

Further, Patent Document 2 discloses a technique of scanning with a signal light in both the horizontal and vertical directions to thereby form a plurality of 2-dimensional tomographic images in the horizontal direction and, based on the plurality of tomographic images, acquiring and imaging 3-dimensional tomographic information of a measurement range. A method for 3-dimensional imaging is, for example, a method of arranging and displaying a plurality of tomographic images in the vertical direction (referred to as stack data or the like), and a method of forming a 3-dimensional image by subjecting a plurality of tomographic images to a rendering process.

Further, Patent Document 3 discloses a configuration of using such an optical image measurement device in the ophthalmic field.

[Patent Document 1] Japanese Unexamined Patent Publication No. 11-325849
[Patent Document 2] Japanese Unexamined Patent Publication No. 2002-139421
[Patent Document 3] Japanese Unexamined Patent Publication No. 2003-543

DISCLOSURE OF THE INVENTION

Problem that the Invention is to Solve

In general, an observer uses an optical image measurement device to observe the condition of an attention site in a measurement object. For example, in the ophthalmic field, major attention sites are the optic papilla and macula of the fundus oculi, and moreover, a lesion site and a treatment site.

Since a conventional optical image measurement device measures both an attention site and other sites with the same accuracy (resolution), a problem as described below may occur. In order to closely observe the condition of an attention site, it is necessary to set high accuracy. Therefore, a measurement on another site is also executed with high accuracy. Consequently, it takes a long time for execution of the measurement, and bodily and physical burden on a patient is great. On the other hand, when a measurement is executed with accuracy for other sites, the accuracy for an attention site is insufficient, and the condition of the attention site cannot be grasped in detail.

The present invention was made for solving the abovementioned problem, and an object of the present invention is to provide an optical image measurement device that is capable of quickly acquiring a highly accurate image of an attention site in a measurement object, and also provide a program that controls the optical measurement device.

Means for Solving the Problem

In order to achieve the abovementioned object, in a first aspect of the present invention, an optical image measurement device, which has: an interference-light generator configured to split a low-coherence light into a signal light and a reference light and superimpose the signal light propagated through a measurement object and the reference light propagated through a reference object to generate an interference light; a detector configured to detect the generated interference light; and an image forming part configured to form an image of the measurement object based on a detection result from the detector, comprises: a scanner configured to scan the measurement object with the signal light; and a controller configured to control the scanner to scan with the signal light while changing a scan interval, in execution of a series of scans with the signal light.

In a second aspect of the present invention, the optical image measurement device according to the first aspect further comprises a designating part configured to designate a region of interest in the image of the measurement object, wherein the controller is configured to control to scan with the signal light so that a scan interval in a partial region of the measurement object including an attention site corresponding to the designated region of interest is smaller than a scan interval in a region other than the partial region.

In a third aspect of the present invention, the optical image measurement device according to the second aspect is characterized in that the designating part includes an extracting part configured to analyze the image of the measurement object and extracts the region of interest.

In a fourth aspect of the present invention, the optical image measurement device according to the third aspect is characterized in that: the measurement object is a fundus oculi; and the extracting part is configured to extract an image region at a predetermined distance from an image position corresponding to an optic papilla of the fundus oculi as the region of interest.

In a fifth aspect of the present invention, the optical image measurement device according to the third aspect is characterized in that: the measurement object is a fundus oculi; and the extracting part is configured to extract an image region at a predetermined distance from an image position corresponding to a macula of the fundus oculi as the region of interest.

In a sixth aspect of the present invention, the optical image measurement device according to the fourth aspect is characterized in that the extracting part is configured to analyze an image of the fundus oculi to specify the image position, and extract an image region at the predetermined distance from the specified image position as the region of interest.

In a seventh aspect of the present invention, the optical image measurement device according to the fifth aspect is characterized in that the extracting part is configured to analyze an image of the fundus oculi to specify the image position, and extract an image region at the predetermined distance from the specified image position as the region of interest.

In an eighth aspect of the present invention, the optical image measurement device according to the fourth aspect is characterized in that: the designating part includes a manipulation part for designating the image position in an image of the fundus oculi; and the extracting part is configured to extract an image region at the predetermined distance from the designated image position as the region of interest.

In a ninth aspect of the present invention, the optical image measurement device according to the fifth aspect is characterized in that: the designating part includes a manipulation part for designating the image position in an image of the fundus oculi; and the extracting part is configured to extract an image region at the predetermined distance from the designated image position as the region of interest.

In a tenth aspect of the present invention, the optical image measurement device according to the sixth aspect is characterized in that the designating part includes an imaging part configured to capture a 2-dimensional image of a surface of the fundus oculi as the image of the fundus oculi.

In an eleventh aspect of the present invention, the optical image measurement device according to the seventh aspect is characterized in that the designating part includes an imaging part configured to capture a 2-dimensional image of a surface of the fundus oculi as the image of the fundus oculi.

In a twelfth aspect of the present invention, the optical image measurement device according to the eighth aspect is characterized in that the designating part includes an imaging part configured to capture a 2-dimensional image of a surface of the fundus oculi as the image of the fundus oculi.

In a thirteenth aspect of the present invention, the optical image measurement device according to the ninth aspect is characterized in that the designating part includes an imaging part configure to capture a 2-dimensional image of a surface of the fundus oculi as the image of the fundus oculi.

In a fourteenth aspect of the present invention, the optical image measurement device according to the second aspect is characterized in that: the measurement object is an eye; the optical image measurement device further comprises a projecting part configured to project a fixation target for fixing at one of two or more fixation positions, onto the eye, and a scan designating part for designating a scanning pattern of the signal light on the eye; and the designating part is configured to designate the region of interest based on the fixation position by the projecting part and the designated scanning pattern.

In a fifteenth aspect of the present invention, the optical image measurement device according to the second aspect is characterized in that the designating part includes a manipulation part for designating the region of interest.

In a sixteenth aspect of the present invention, the optical image measurement device according to the fifteenth aspect is characterized in that: the designating part includes an imaging part configured to capture a 2-dimensional image of a surface of the fundus oculi as the image of the measurement object, and a display configured to display the captured 2-dimensional image; and the manipulation part is used for designating the region of interest in the displayed 2-dimensional image.

In a seventeenth aspect of the present invention, the optical image measurement device according to the first aspect is characterized in that the controller includes a storage configured to store information representing the scan interval of the signal light in the series of scans, and configured to control to scan with the signal light based on the stored information, in execution of a new series of scans with the signal light.

In an eighteenth aspect of the present invention, the optical image measurement device according to the first aspect is characterized in that: the controller includes a storage configured to store information representing the scan interval of the signal light in the series of scans; and the image forming part is configured to form a 3-dimensional image of the measurement object based on the stored information.

In a nineteenth aspects of the present invention, a program is configured to control an optical image measurement device that has: an interference-light generator configured to split a low-coherence light into a signal light and a reference light and superimpose the signal light propagated through a measurement object and the reference light propagated through a reference object to generate an interference light; a detector configured to detect the generated interference light; a scanner configured to scan the measurement object with the signal light; and a computer, and that forms an image of the measurement object based on a detection result from the detector, wherein the program makes the computer function as a controller configured to control the scanner to scan with the signal light while changing a scan interval, in execution of a series of scans with the signal light.

Effect of the Invention

According to the present invention, it is possible to execute a series of scans with a signal light while changing a scan interval.

Therefore, it is possible to set a scan interval in an attention site (and a partial region including the attention site) in a measurement object so as to be smaller than a scan interval in other regions, and consequently, it is possible to quickly acquire a highly accurate image of the attention site.

BRIEF DESCRIPTION OF THE DRAWINGS

FIG. 7A shows an example of the scanning pattern of the signal light when the fundus oculi is seen from the incident side of the signal light into an eye. FIG. 7B shows an example of an arrangement pattern of scanning points on each scanning line.

FIG. 13 is a flowchart showing an example of a usage pattern of the embodiment of the fundus oculi observation device functioning as the optical image measurement device according to the present invention.

Figure 1:
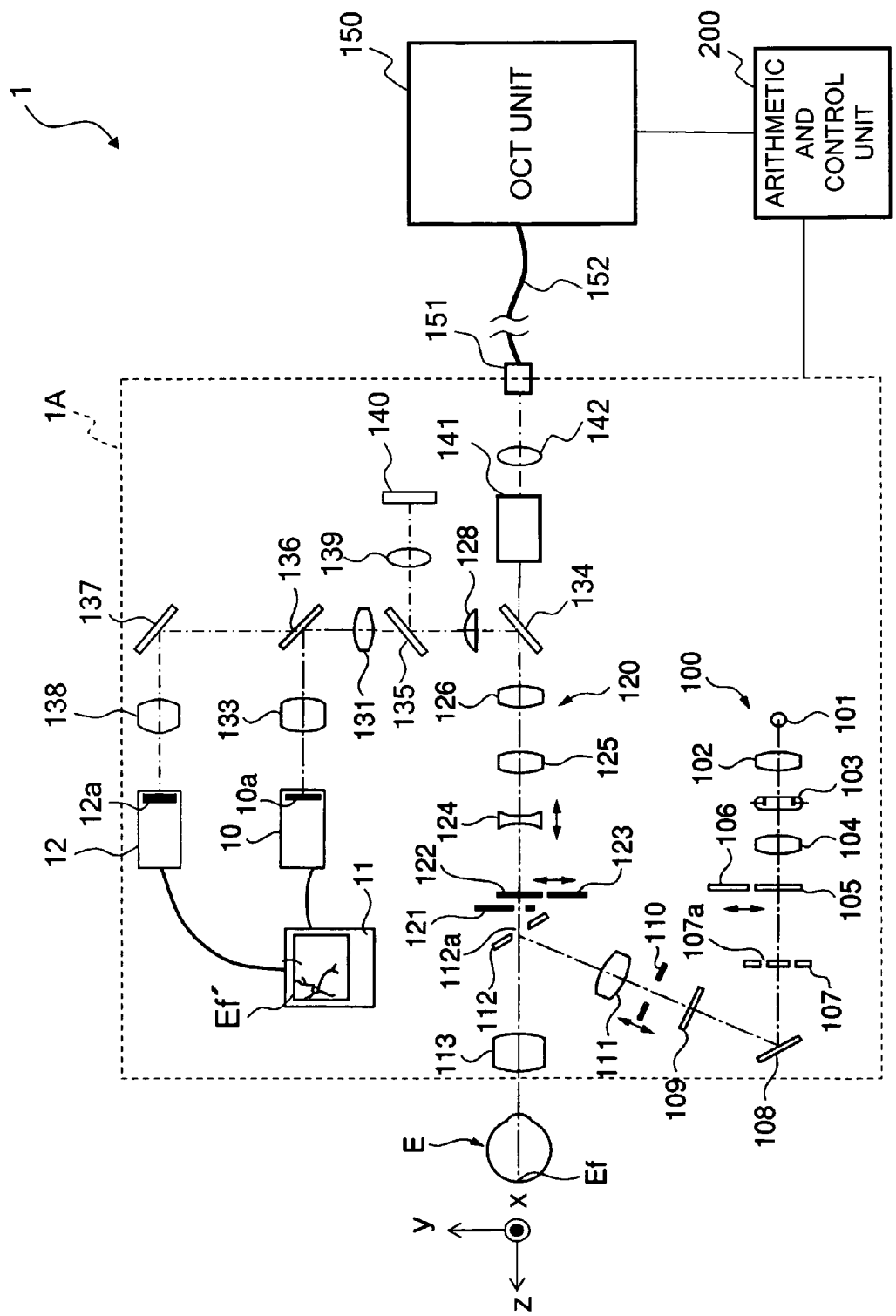
FIG. 1 is a schematic configuration diagram showing an example of the entire configuration in an embodiment of a fundus oculi observation device functioning as the optical image measurement device according to the present invention.

DESCRIPTION OF REFERENCE NUMERALS AND SYMBOLS 1 fundus oculi observation device (optical image measurement device)
1A retinal camera unit
140 LCD
141 scan unit
141A, 141B Galvano mirrors
150 OCT unit
160 low-coherence light source
162 optical coupler
174 reference mirror
180 spectrometer
184 CCD
200 arithmetic and control unit
204a control program
210 controller
211 main controller
212 storage
213 scan setting part
220 image forming part
230 image processor
231 image extracting part
240 user interface
240A display
240B manipulation part
241, 242 mirror drive mechanisms
R scanning region
Ri(i=1~m) scanning line
Rij(i=1~m, j=1~n) scanning point
E eye
Ef fundus oculi

BEST MODE FOR CARRYING OUT THE INVENTION

An example of a preferred embodiment of an optical image measurement device and a program for controlling the optical image measurement device according to the present invention will be described in detail with reference to the drawings.

The present invention relates to the OCT technology of forming an image based on an interference light obtained by superimposing a light propagated through a measurement object and a light propagated through a reference object. In particular, the present invention is favorably utilized for Fourier-domain OCT or swept source OCT of scanning a measurement object with a light to execute a measurement.

[Device Configuration]

First, with reference to FIGS. 1 through 6, the configuration in an embodiment of the optical image measurement device according to the present invention will be described. The optical image measurement device according to this embodiment is used in the ophthalmic field. FIG. 1 shows an example of the entire configuration of a fundus oculi observation device 1 having a function as the optical image measurement device according to the present invention.

Figure 2:
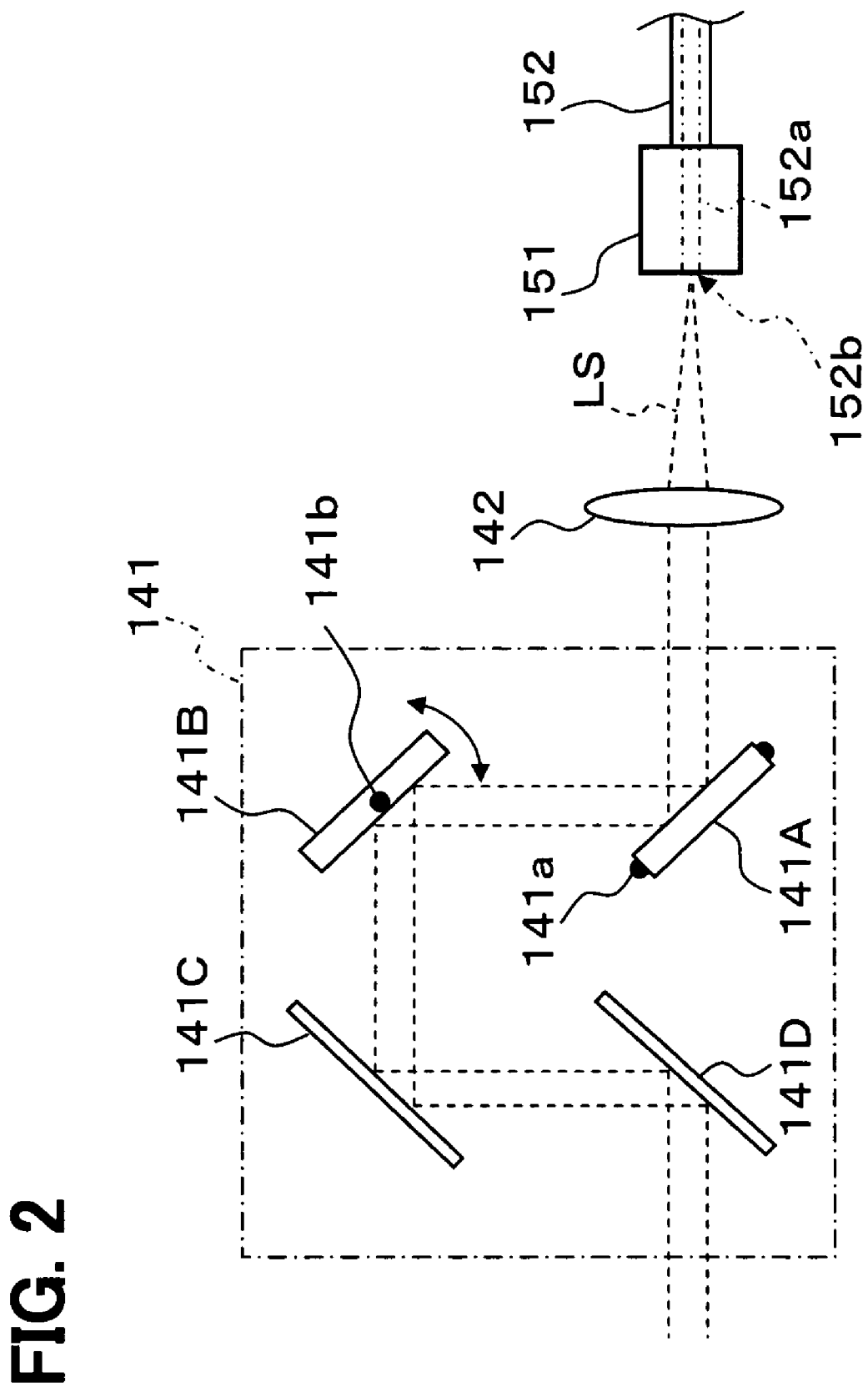
FIG. 2 is a schematic configuration diagram showing an example of the configuration of a scan unit installed in a retinal camera unit in the embodiment of the fundus oculi observation device functioning as the optical image measurement device according to the present invention.
Figure 3:
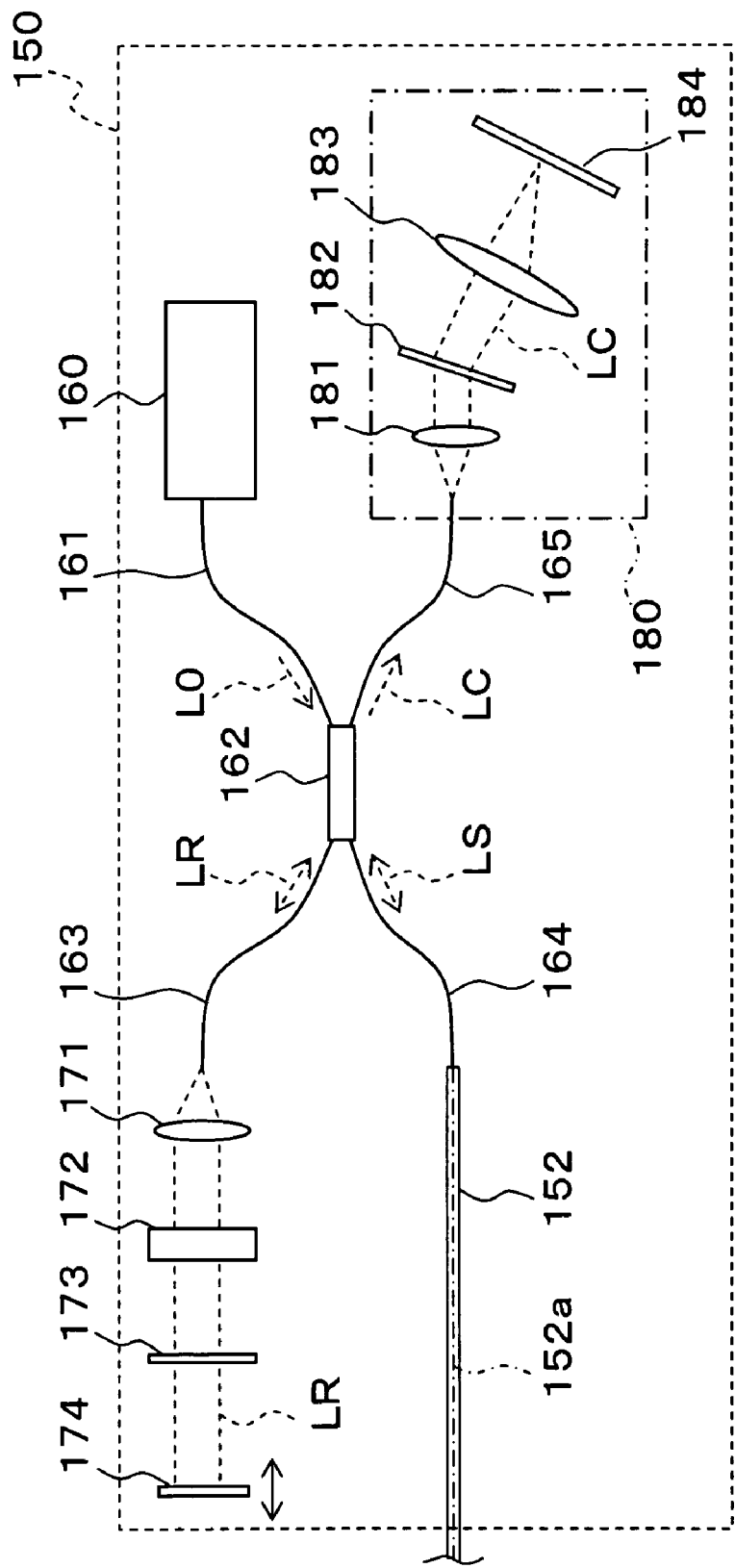
FIG. 3 is a schematic configuration diagram showing an example of the configuration of an OCT unit in the embodiment of the fundus oculi observation device functioning as the optical image measurement device according to the present invention.
Figure 4:
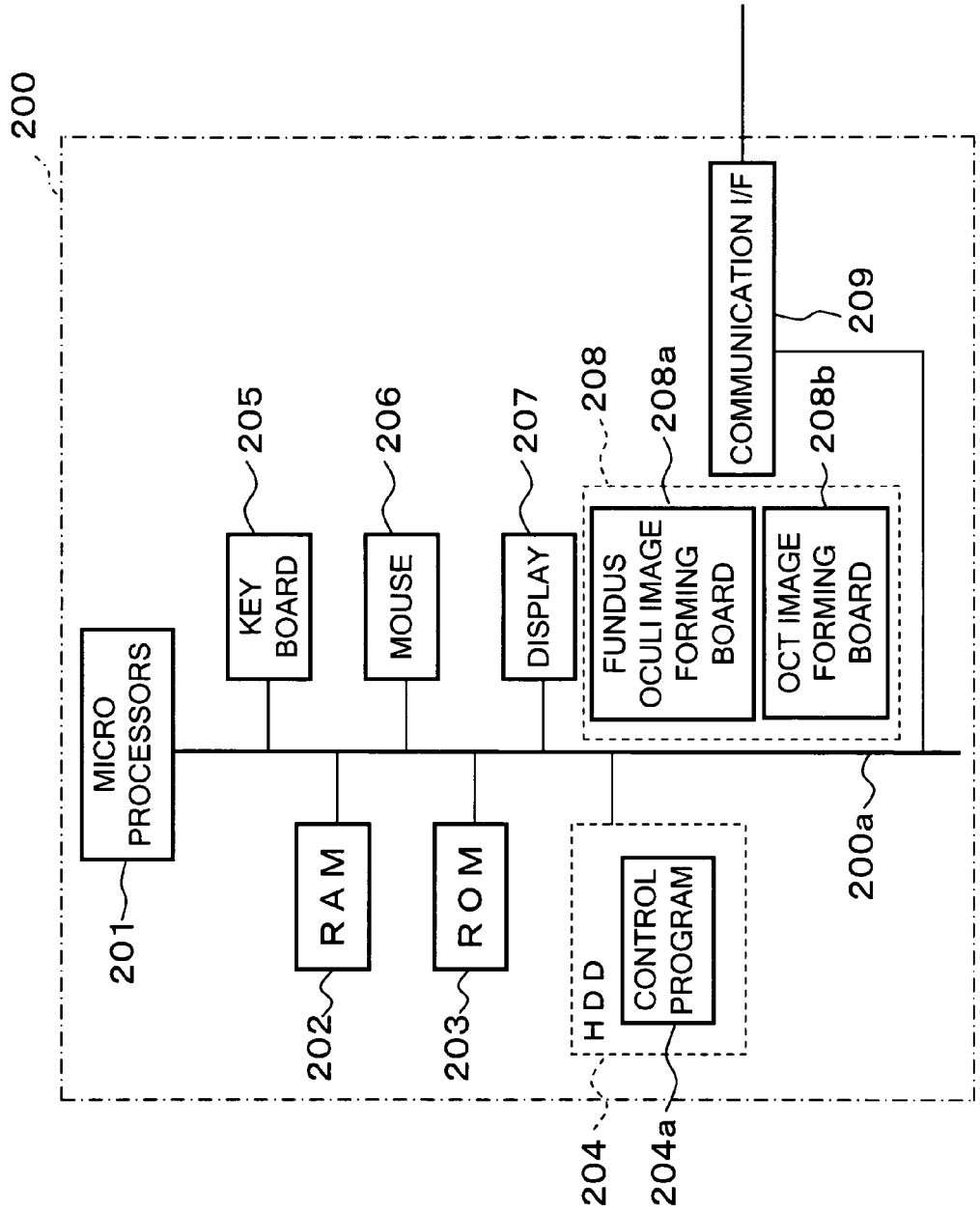
FIG. 4 is a schematic block diagram showing an example of the hardware configuration of an arithmetic and control unit in the embodiment of the fundus oculi observation device functioning as the optical image measurement device according to the present invention.
Figure 5:
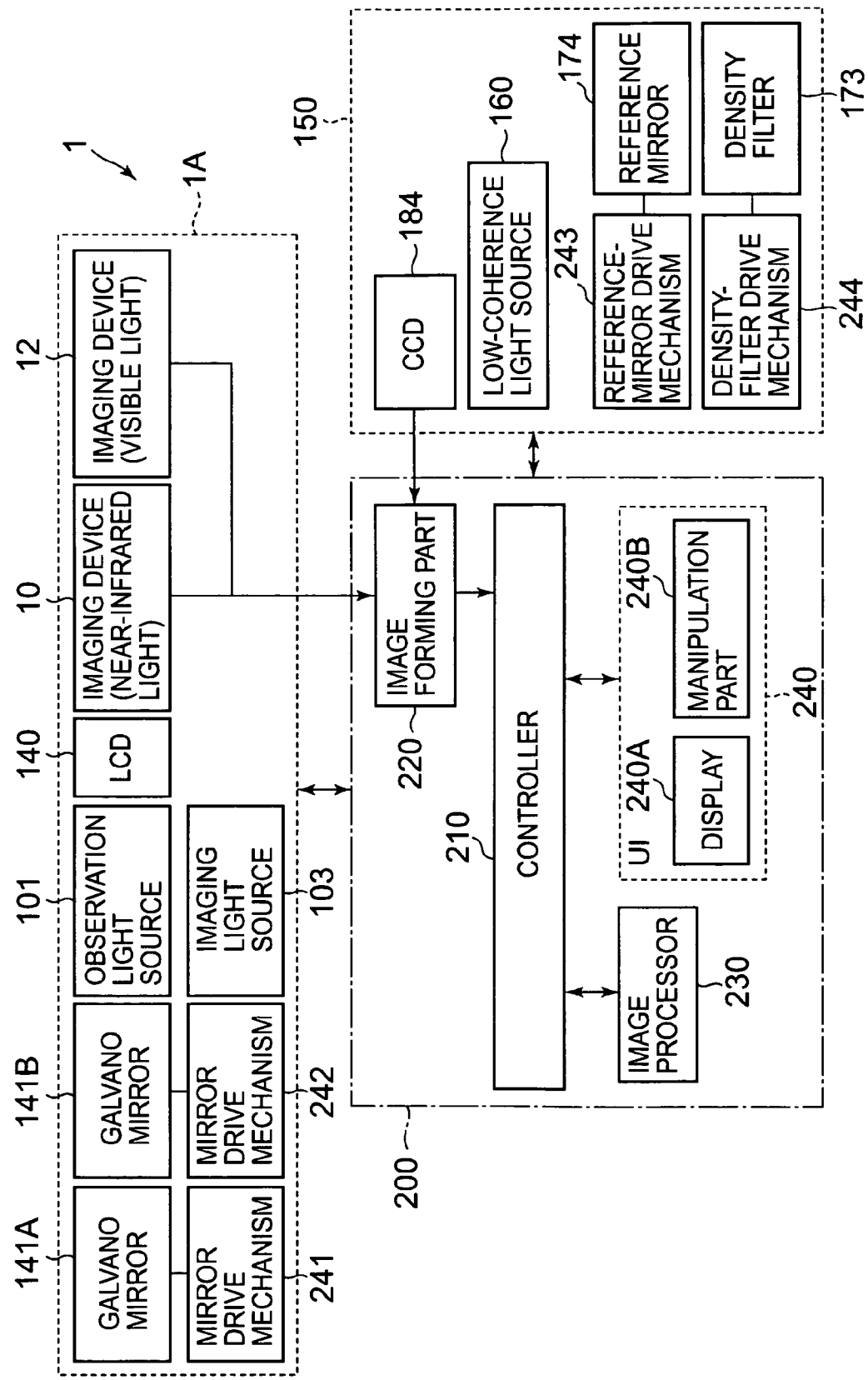
FIG. 5 is a schematic block diagram showing an example of the configuration of a control system in the embodiment of the fundus oculi observation device functioning as the optical image measurement device according to the present invention.
Figure 6:
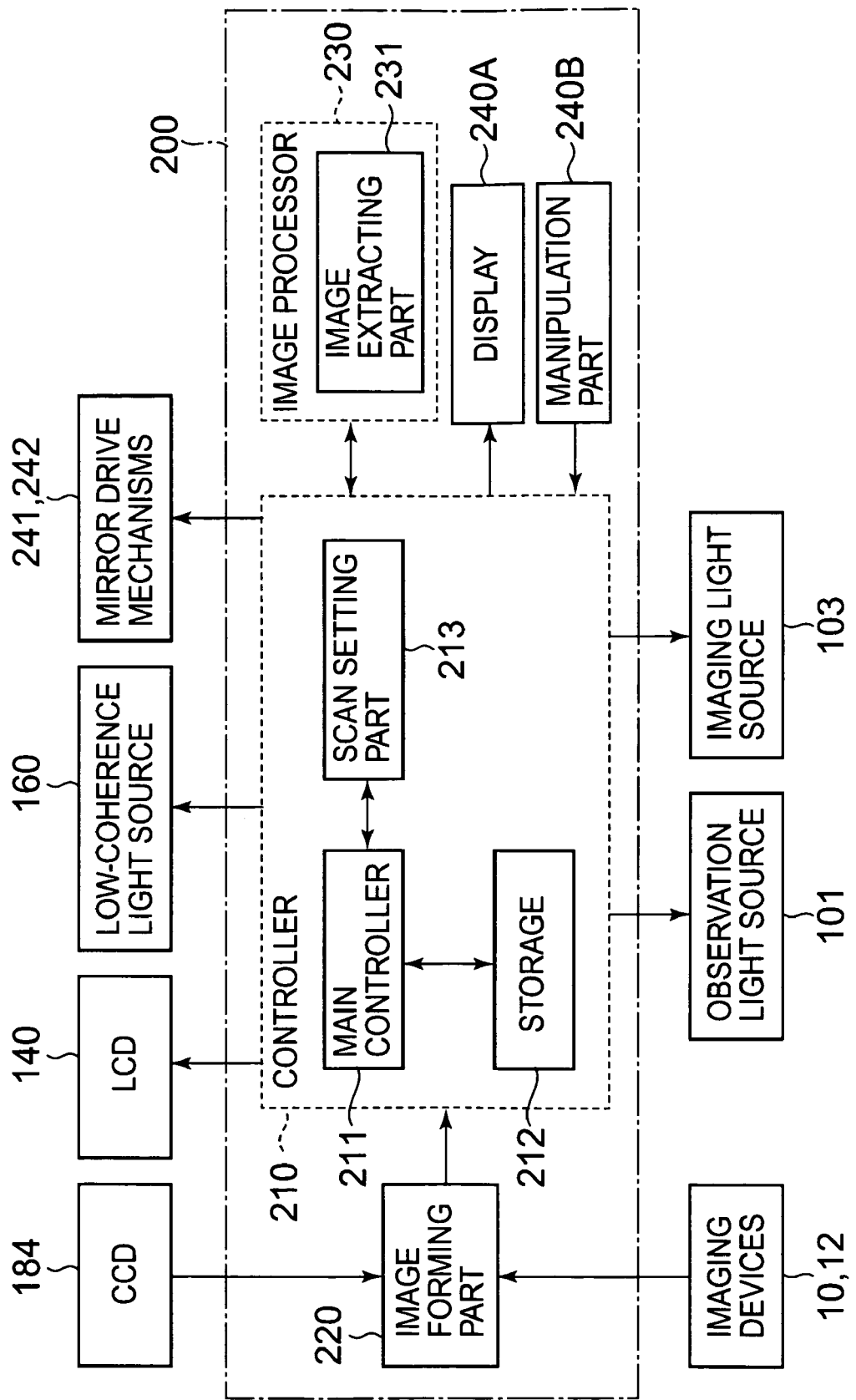
FIG. 6 is a schematic block diagram showing an example of the configuration of a control system in the embodiment of the fundus oculi observation device functioning as the optical image measurement device according to the present invention.

FIG. 2 shows an example of the configuration of a scan unit 141 in a retinal camera unit 1A. FIG. 3 shows an example of the configuration of an OCT unit 150. FIG. 4 shows an example of the hardware configuration of an arithmetic and control unit 200. FIGS. 5 and 6 show an example of the configuration of a control system of the fundus oculi observation device 1.

[Entire Configuration]

The fundus oculi observation device 1 includes the retinal camera unit 1A, the OCT unit 150, and the arithmetic and control unit 200 as shown in FIG. 1. The retinal camera unit 1A has almost the same optical system as a conventional retinal camera that captures a 2-dimensional image of the fundus oculi surface. The OCT unit 150 houses an optical system that functions as the optical image measurement device. The arithmetic and control unit 200 is provided with a computer that executes various kinds of arithmetic processes, control processes and so on.

To the OCT unit 150, one end of a connection line 152 is attached. A connector part 151 connecting the connection line 152 to the retinal camera unit 1A is attached to the other end of the connection line 152. A conductive optical fiber runs through inside the connection line 152. Thus, the OCT unit 150 and the retinal camera unit 1A are optically connected via the connection line 152.

[Configuration of Retinal Camera Unit]

The retinal camera unit 1A is used for forming a 2-dimensional image of the surface of the fundus oculi of an eye based on optically acquired data (data detected by an imaging device 10 or 12). The 2-dimensional image of the surface of the fundus oculi refers to a color image or monochrome image of the surface of the fundus oculi, a fluorescent image (e.g., a fluorescein angiography image and an indocyanine green fluorescent image) and the like. Like the conventional retinal camera, the retinal camera unit 1A is provided with an illumination optical system 100 that illuminates a fundus oculi Ef, and an imaging optical system 120 that guides the fundus oculi reflection light of the illumination light to the imaging device 10.

The imaging device 10 in the imaging optical system 120 detects an illumination light having a wavelength of a near-infrared region, which will be described in detail later. The imaging optical system 120 is also provided with the imaging device 12 detecting an illumination light having a wavelength of a visible region. The imaging optical system 120 guides a signal light coming from the OCT unit 150 to the fundus oculi Ef and guides the signal light propagated through the fundus oculi Ef to the OCT unit 150.

The illumination optical system 100 includes: an observation light source 101; a condenser lens 102; an imaging light source 103; a condenser lens 104; exciter filters 105 and 106; a ring transparent plate 107; a mirror 108; an LCD (Liquid Crystal Display) 109; an illumination diaphragm 110; a relay lens 111; an aperture mirror 112; and an objective lens 113.

The observation light source 101 outputs an illumination light having a wavelength of a visible region included in a range of about 400 nm to 700 nm, for example. The imaging light source 103 outputs an illumination light having a wavelength of a near-infrared region included in a range of about 700 nm to 800 nm, for example. The near-infrared light outputted from the imaging light source 103 is set so as to have a shorter wavelength than the light used by the OCT unit 150 (described later).

The imaging optical system 120 includes: the objective lens 113; the aperture mirror 112 (an aperture 112a thereof); an imaging diaphragm 121; barrier filters 122 and 123; a variable magnifying lens 124; a relay lens 125; an imaging lens 126; a dichroic mirror 134; a field lens 128; a half mirror 135; a relay lens 131; a dichroic mirror 136; an imaging lens 133; the imaging device 10 (image pick-up element 10a); a reflection mirror 137; an imaging lens 138; the imaging device 12 (image pick-up element 12a); a lens 139; and an LCD 140.

Further, the imaging optical system 120 includes: a dichroic mirror 134; a half mirror 135; a dichroic mirror 136; a reflection mirror 137; an imaging lens 138; a lens 139; and an LCD 140.

The dichroic mirror 134 is configured to reflect the fundus oculi reflection light (having a wavelength included in the range of about 400 nm to 800 nm) of the illumination light coming from the illumination optical system 100, and to transmit a signal light LS (having a wavelength included in the range of, for example, about 800 nm to 900 nm; described later) coming from the OCT unit 150.

The dichroic mirror 136 is configured to transmit the illumination light having a wavelength of the visible region coming from the illumination optical system 100 (a visible light having a wavelength of about 400 nm to 700 nm outputted from the observation light source 101), and to reflect the illumination light having a wavelength of the near-infrared region (a near-infrared light having a wavelength of about 700 nm to 800 nm outputted from the imaging light source 103).

The LCD 140 displays a fixation target (an internal fixation target) for fixing the eye E. A light from the LCD 140 is reflected by the half mirror 135 after being focused by the lens 139, and is reflected by the dichroic mirror 136 after propagated through the field lens 128. Furthermore, this light is propagated through the imaging lens 126, the relay lens 125, the variable magnifying lens 124, the (aperture 112a of) aperture mirror 112, the objective lens 113, and so on, and enters into the eye E. Consequently, the internal fixation target is projected on the fundus oculi Ef of the eye E.

The LCD 140 that displays the internal fixation target and the aforementioned optical system that projects the displayed internal fixation target onto the eye E are an example of the "projecting part" of the present invention. The projecting part may be configured outside the retinal camera unit 1A and to project the fixation target onto the eye E.

The image pick-up element 10a is an image pick-up element such as a CCD (Charge Coupled Device) and a CMOS (Complementary Metal Oxide Semiconductor) installed in the imaging device 10 such as a TV camera, and particularly detects a light having a wavelength of the near-infrared region. In other words, the imaging device 10 is an infrared TV camera that detects a near-infrared light. The imaging device 10 outputs video signals as the result of detection of the near-infrared light.

A touch panel monitor 11 displays a 2-dimensional image of the surface of the fundus oculi Ef (a fundus oculi image Ef'), based on the video signals. The video signals are sent to the arithmetic and control unit 200, and the fundus oculi image is displayed on the display (described later).

For imaging the fundus oculi by the imaging device 10, for example, an illumination light outputted from the imaging light source 103 of the illumination optical system 100 and having a wavelength of the near-infrared region is used.

On the other hand, the image pick-up element 12a is an image pick-up element such as a CCD and a CMOS installed in the imaging device 12 such as a TV camera, and particularly detects a light having a wavelength of the visible region. That is to say, the imaging device 12 is a TV camera that detects a visible light. The imaging device 12 outputs video signals as the result of detection of the visible light.

The touch panel monitor 11 displays a 2-dimensional image of the surface of the fundus oculi Ef (the fundus oculi image Ef'), based on the video signals. The video signals are sent to the arithmetic and control unit 200, and the fundus oculi image is displayed on the display (described later).

For imaging the fundus oculi by the imaging device 12, for example, an illumination light outputted from the observation light source 101 of the illumination optical system 100 and having a wavelength of the visible region is used.

The retinal camera unit 1A is provided with a scan unit 141 and a lens 142. The scan unit 141 includes a component for scanning a projection position on the fundus oculi Ef with a light outputted from the OCT unit 150 (the signal light LS; described later). The scan unit 141 is an example of the "scanner" of the present invention.

The lens 142 makes the signal light LS guided from the OCT unit 150 through the connection line 152 enter into the scan unit 141 in the form of a parallel light flux. Moreover, the lens 142 focuses the fundus oculi reflection light of the signal light LS propagated through the scan unit 141.

FIG. 2 shows an example of the configuration of the scan unit 141. The scan unit 141 includes Galvano mirrors 141A and 141B, and reflection mirrors 141C and 141D.

The Galvano mirrors 141A and 141B are reflection mirrors disposed so as to be rotatable about rotary shafts 141a and 141b, respectively. The Galvano mirrors 141A and 141B are rotated about the rotary shafts 141a and 141b, respectively, by drive mechanisms described later (mirror drive mechanisms 241 and 242 shown in FIG. 5). Consequently, the reflection faces (the faces reflecting the signal light LS) of the Galvano mirrors 141A and 141B are turned around, respectively.

The rotary shafts 141a and 141b are arranged orthogonally to each other. In FIG. 2, the rotary shaft 141a of the Galvano mirror 141A is arranged in parallel to the paper face. On the other hand, the rotary shaft 141b of the Galvano mirror 141B is arranged in the orthogonal direction to the paper face.

That is to say, the Galvano mirror 141B is formed so as to be rotatable in the directions indicated by an arrow pointing in both directions in FIG. 2, whereas the Galvano mirror 141A is formed so as to be rotatable in the directions orthogonal to the arrow pointing in both the directions. Consequently, the Galvano mirrors 141A and 141B act so as to turn directions of reflecting the signal light LS into directions orthogonal to each other. As seen from FIGS. 1 and 2, a scan with the signal light LS is performed in the x-direction when the Galvano mirror 141A is rotated, and a scan with the signal light LS is performed in the y-direction when the Galvano mirror 141B is rotated.

The signal lights LS reflected by the Galvano mirrors 141A and 141B are reflected by reflection mirrors 141C and 141D, thereby traveling in the same direction as having entered into the Galvano mirror 141A.

An end face 152b of the optical fiber 152a inside the connection line 152 is arranged facing the lens 142. The signal light LS emitted from the end face 152b travels expanding its beam diameter toward the lens 142, and is made into a parallel light flux by the lens 142. On the contrary, the signal light LS propagated through the fundus oculi Ef is focused to the end face 152b by the lens 142, and enters into the optical fiber 152a.

[Configuration of OCT Unit]

Next, the configuration of the OCT unit 150 will be described with reference to FIG. 3. The OCT unit 150 is a device for forming a tomographic image of the fundus oculi based on optically obtained data (data detected by a CCD 184 described later).

The OCT unit 150 has almost the same optical system as a conventional optical image measurement device. That is to say, the OCT unit 150 splits a low-coherence light into a reference light and a signal light and superimposes the signal light propagated through an eye with the reference light propagated through a reference object, thereby generating and detecting an interference light. The result of this detection (a detection signal) is inputted to the arithmetic and control unit 200. The arithmetic and control unit 200 forms a tomographic image of the eye by analyzing the detection signal.

A low-coherence light source 160 is composed of a broadband light source, such as a super luminescent diode (SLD) and a light emitting diode (LED), which outputs a low-coherence light L0. The low-coherence light L0 is, for example, a light including a light with a wavelength of the near-infrared region and having a temporal coherence length of approximately several tens of micrometers.

The low-coherence light L0 has a longer wavelength than the illumination light of the retinal camera unit 1A (wavelength of about 400 nm to 800 nm), for example, a wavelength included in a range of about 800 nm to 900 nm.

The low-coherence light L0 outputted from the low-coherence light source 160 is guided to an optical coupler 162 through an optical fiber 161. The optical fiber 161 is composed of, for example, a single mode fiber or a PM (Polarization maintaining) fiber. The optical coupler 162 splits the low-coherence light L0 into a reference light LR and the signal light LS.

Although the optical coupler 162 acts as both a part (splitter) for splitting a light and a part (coupler) for superimposing lights, it will be herein referred to as an "optical coupler" idiomatically.

The reference light LR generated by the optical coupler 162 is guided by an optical fiber 163 composed of a single mode fiber or the like, and emitted from the end face of the fiber. Furthermore, the reference light LR is made into a parallel light flux by a collimator lens 171, propagated through a glass block 172 and a density filter 173, and reflected by a reference mirror 174. The reference mirror 174 is an example of the "reference object" of the present invention.

The reference light LR reflected by the reference mirror 174 is again propagated through the density filter 173 and the glass block 172, focused to the fiber end face of the optical fiber 163 by the collimator lens 171, and guided to the optical coupler 162 through the optical fiber 163.

The glass block 172 and the density filter 173 act as a delaying part for matching the optical path lengths (optical distances) of the reference light LR and the signal light LS, and also as a dispersion compensation part for matching the dispersion characteristics of the reference light LR and the signal light LS.

The density filter 173 also acts as a dark filter that reduces the amount of the reference light, and is composed of a rotating ND (neutral density) filter, for example. The density filter 173 acts so as to change the reduction amount of the reference light LR by being rotary driven by a drive mechanism including a drive unit such as a motor (a density-filter drive mechanism 244 described later; refer to FIG. 5). Consequently, it is possible to change the amount of the reference light LR contributing to generation of an interference light LC.

Further, the reference mirror 174 is configured to move in the traveling direction of the reference light LR (the direction of the arrow pointing both sides shown in FIG. 3). Thus, it is possible to ensure the optical path length of the reference light LR according to the axial length of the eye E, the working distance (the distance between the objective lens 113 and the eye E), and so on. Moreover, it is possible to acquire an image of any depth position of the fundus oculi Ef, by moving the reference mirror 174. The reference mirror is moved by a drive mechanism (a reference-mirror drive mechanism 243 described later; refer to FIG. 5) including a driver such as a motor.

On the other hand, the signal light LS generated by the optical coupler 162 is guided to the end of the connection line 152 through an optical fiber 164 composed of a single mode fiber or the like. The optical fiber 152a runs inside the connection line 152. The optical fiber 164 and the optical fiber 152a may be composed of one optical fiber, or may be integrally formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is guided through the inside of the connection line 152 and led to the retinal camera unit 1A.

Furthermore, the signal light LS is projected to the eye E through the lens 142, the scan unit 141, the dichroic mirror 134, the imaging lens 126, the relay lens 125, the variable magnifying lens 124, the imaging diaphragm 121, the aperture 112a of the aperture mirror 112 and the objective lens 113. The barrier filter 122 and 123 are retracted from the optical path in advance, respectively, when the signal light LS is projected to the eye E.

The signal light LS having entered into the eye E forms an image on the fundus oculi Ef and is then reflected. In this case, the signal light LS is not only reflected on the surface of the fundus oculi Ef, but also scattered at the refractive index boundary after reaching the deep area of the fundus oculi Ef. Therefore, the signal light LS propagated through the fundus oculi Ef contains information reflecting the morphology of the surface of the fundus oculi Ef and information reflecting the state of backscatter at the refractive index boundary of the deep area tissue of the fundus oculi Ef. This light may be simply referred to as the "fundus oculi reflection light of the signal light LS."

The fundus oculi reflection light of the signal light LS reversely travels along the abovementioned path within the retinal camera unit 1A, and is focused to the end face 152b of the optical fiber 152a. Then, the signal light LS enters into the OCT unit 150 through the optical fiber 152a, and returns to the optical coupler 162 through the optical fiber 164.

The optical coupler 162 superimposes the signal light LS returned through the eye E and the reference light LR reflected by the reference mirror 174, thereby generating the interference light LC.

The generated interference light LC is guided into a spectrometer 180 through an optical fiber 165 composed of a single mode fiber or the like.

Although a Michelson-type interferometer is adopted in this embodiment, it is possible to properly employ a Mach Zender type or the like, and any type of interferometer.

The "interference-light generator" of the present invention includes, for example, an optical coupler 162, an optical member on the optical path of the signal light LS (i.e., an optical member placed between the optical coupler 162 and the eye E), and an optical member on the optical path of the reference light LR (i.e., an optical member placed between the optical coupler 162 and the reference mirror 174), and specifically, includes an interferometer equipped with the optical coupler 162, the optical fibers 163 and 164, and the reference mirror 174.

The spectrometer 180 includes a collimator lens 181, a diffraction grating 182, an image forming lens 183, and a CCD 184.

The diffraction grating 182 may be a transmission-type diffraction grating that transmits light, or may be a reflection-type diffraction grating that reflects light. Moreover, it is also possible to use, instead of the CCD 184, another photodetecting element such as a CMOS.

The interference light LC having entered into the spectrometer is split (resolved into spectra) by the diffraction grating 182 after made into a parallel light flux by the collimator lens 181. The split interference light LC is formed into an image on the image pick-up face of the CCD 184 by the image forming lens 183. The CCD detects the respective spectra of the split interference light LC and converts to electrical detection signals, and outputs the detection signals to the arithmetic and control unit 200. The CCD 184 is an example of the "detector" of the present invention.

[Configuration of Arithmetic and Control Unit]

Next, the configuration of the arithmetic and control unit 200 will be described. The arithmetic and control unit 200 analyzes detection signals inputted from the CCD 184 of the OCT unit 150, and forms a tomographic image of the fundus oculi Ef. This analysis method is the same as the conventional Fourier Domain OCT method.

Further, the arithmetic and control unit 200 forms a 2-dimensional image showing the morphology of the surface of the fundus oculi Ef, based on the video signals outputted from the imaging devices 10 and 12 of the retinal camera unit 1A.

Furthermore, the arithmetic and control unit 200 controls each part of the retinal camera unit 1A and the OCT unit 150.

As control of the retinal camera unit 1A, the arithmetic and control unit 200 executes, for example: control of output of the illumination light by the observation light source 101 or the imaging light source 103; control of insertion/retraction operations of the exciter filters 105 and 106 or the barrier filters 122 and 123 to/from the optical path; control of the operation of a display device such as the LCD 140; control of movement of the illumination diaphragm 110 (control of the diaphragm value); control of the diaphragm value of the imaging diaphragm 121; and control of movement of the variable magnifying lens 124 (control of the magnification). Moreover, the arithmetic and control unit 200 executes control of the operation of the Galvano mirrors 141A and 141B.

On the other hand, as control of the OCT unit 150, the arithmetic and control unit 200 executes, for example: control of output of the low-coherence light L0 by the low-coherence light source 160; control of movement of the reference mirror 174; control of the rotary operation of the density filter 173 (the operation of changing the reduction amount of the reference light LR); and control of the accumulation time of the CCD 184.

The hardware configuration of the arithmetic and control unit 200 will be described with reference to FIG. 4.

The arithmetic and control unit 200 is provided with a similar hardware configuration to that of a conventional computer. To be specific, the arithmetic and control unit 200 includes: a microprocessor 201, a RAM 202, a ROM 203, a hard disk drive (HDD) 204, a keyboard 205, a mouse 206, a display 207, an image forming board 208, and a communication interface (I/F) 209. These parts are connected via a bus 200a.

The microprocessor 201 includes a CPU (Central Processing Unit), an MPU (Micro Processing Unit) or the like. The microprocessor 201 executes operations characteristic to this embodiment, by loading a control program 204a stored in the hard disk drive 204, onto the RAM 202.

Further, the microprocessor 201 executes control of each part of the device described above, various arithmetic processes, and so on. Further, the microprocessor 201 receives an operation signal from the keyboard 205 or the mouse 206, and executes control of each part of the device in response to the operation content. Furthermore, the microprocessor 201 executes control of a display process by the display 207, control of a transmission/reception process of data and signals by the communication interface 209.

The keyboard 205, the mouse 206 and the display 207 are used as user interfaces in the fundus oculi observation device 1. The keyboard 205 is used as, for example, a device for typing letters, figures, or the like. The mouse 206 is used as a device for performing various input operations to the display screen of the display 207.

Further, the display 207 is a display device such as an LCD and a CRT (Cathode Ray Tube) display, and displays various images like an image of the fundus oculi Ef formed by the fundus oculi observation device 1, or displays various screens such as an operation screen and a set-up screen.

The user interface of the fundus oculi observation device 1 is not limited to the above configuration, and may include a track ball, a control lever, an LCD of touch panel type, a control panel for ophthalmology examinations, and the like. As a user interface, it is possible to employ any configuration having a function of displaying and outputting information and a function of inputting information and operating the device.

The image forming board 208 is a dedicated electronic circuit for forming (image data of) images of the fundus oculi Ef. The image forming board 208 is provided with the fundus oculi image forming board 208a and an OCT image forming board 208b.

The fundus oculi image forming board 208a is a dedicated electronic circuit that forms image data of fundus oculi images based on the video signals from the imaging device 10 and the imaging device 12.

Further, the OCT image forming board 208b is a dedicated electronic circuit that forms image data of tomographic images of the fundus oculi Ef, based on the detection signals from the CCD 184 of the OCT unit 150.

By providing the image forming board 208, it is possible to increase the processing speed of a process for forming fundus oculi images and tomographic images.

The communication interface 209 sends control signals from the microprocessor 201, to the retinal camera unit 1A or the OCT unit 150. Moreover, the communication interface 209 receives video signals from the imaging devices 10 and 12 or detection signals from the CCD 184 of the OCT unit 150, and inputs the signals to the image forming board 208. At this moment, the communication interface 209 operates to input the video signals from the imaging devices 10 and 12, to the fundus oculi image forming board 208a, and input the detection signals from the CCD 184, to the OCT image forming board 208b.

Further, in a case where the arithmetic and control unit 200 is connected to a communication network such as a LAN (Local Area Network) and the Internet, it is possible to configure to be capable of data communication via the communication network, by providing the communication interface 209 with a network adapter like a LAN card or communication equipment like a modem. In this case, by mounting a server accommodating the control program 204a on the communication network, and also configuring the arithmetic and control unit 200 as a client terminal of the server, it is possible to operate the fundus oculi observation device 1.

[Configuration of Control System]

Next, the configuration of the control system of the fundus oculi observation device 1 will be described with reference to FIGS. 5 and 6.

(Controller)

The control system of the fundus oculi observation device 1 is configured mainly having a controller 210 of the arithmetic and control unit 200. The controller 210 includes the microprocessor 201, the RAM 202, the ROM 203, the hard disk drive 204 (the control program 204a), and the communication interface 209.

The controller 210 executes the aforementioned control by the microprocessor 201 that operates based on the control program 204a.

The controller 201 is provided with a main controller 211, a storage 212, and a scan setting part 213. The controller 210 is an example of the "controller" according to the present invention.

The main controller 211 controls the mirror drive mechanisms 241 and 242 to control the positions of the Galvano mirrors 141A and 141B so as to scan the fundus oculi Ef with the signal light LS.

The controller 211 also controls the LCD 140 to display the internal fixation target for fixing the eye E at various fixation positions. An example of the fixation position includes a fixation position for acquiring an image of the optic papilla of the fundus oculi Ef, a fixation position for acquiring an image of the macula, and the like. It is also possible to fix the eye E at an arbitrary fixation position. For that purpose, it is possible to configure so that, for example, the projection position of the internal fixation target onto the eye E can be changed by manipulating the manipulation part 240B. Besides, it is possible to configure so that the projection position of the internal fixation target onto the eye E can be changed based on information of past fixation positions stored in the storage 212, or the like.

Further, the main controller 211 executes controls of the respective parts of the device, such as control of the low-coherence light source 160 to turn on/off, control of the CCD 184, control of the density-filter drive mechanism 244 to rotate the density filter 173, control of the reference-mirror drive mechanism 243 to move the reference mirror 174 in the traveling direction of the reference light LR, and control of the observation light source 101 and the imaging light source 103 to turn on/off.

Further, the main controller 211 controls a display 240A of the user interface (UI) 240 to display two kinds of images captured by the fundus oculi observation device 1, i.e., the fundus oculi image Ef' and a tomographic image. These images may be displayed on the display 240A separately, or may be displayed side by side.

The storage 212 stores image data formed by an image forming part 220 and an image processor 230. The storage 212 also stores various data such as information set by the scan setting part 213. A process of writing the data into the storage 212 and a process of reading out the data from the storage 212 are executed by the main controller 211.

The scan setting part 213 sets information regarding a scan with the signal light LS. For example, the scan setting part 213 sets scanning points, scanning lines and scanning regions of the signal light LS. Details of this process will be described later.

(Image Forming Part)

The image forming part 220 forms image data of the fundus oculi image Ef' based on the video signals outputted from the imaging devices 10 and 12. The image forming part 220 also forms image data of the tomographic image of the fundus oculi Ef based on the detection signals outputted from the CCD 184 of the OCT unit 150.

The image forming part 220 includes the image forming board 208, the communication interface 209, and so on. In this specification, "image" may be identified with "image data" corresponding thereto.

(Image Processor)

The image processor 230 applies various kinds of image processing and analysis processes to image data of images formed by the image forming part 220. For example, the image processor 230 executes various kinds of correction processes such as luminance correction and dispersion correction of the images.

Further, the image processor 230 applies an interpolation process of interpolating pixels between tomographic images formed by the image forming part 220 to the tomographic images, thereby forming image data of a 3-dimensional image of the fundus oculi Ef.

Image data of a 3-dimensional image is image data made by assigning pixel values to each of a plurality of voxels arranged 3-dimensionally, and is referred to as volume data, voxel data, or the like. In the case of displaying an image based on volume data, the image processor 230 executes a rendering process (such as volume rendering and MIP (Maximum Intensity Projection)) on this volume data, and forms image data of a pseudo 3-dimensional image seen from a specific view direction. On a display device such as the display 207, the pseudo 3-dimensional image based on the image data is displayed.

Further, the image processor 230 is also capable of forming stack data of a plurality of tomographic images. Stack data is image data that can be obtained by arranging a plurality of tomographic images acquired along a plurality of scanning lines based on the positional relationship of the scanning lines.

The image processor 230 is provided with an image extracting part 231. The image extracting part 231 analyzes an image of the fundus oculi Ef and extracts a region of interest. The image of the fundus oculi Ef may be a 2-dimensional image of the surface of the fundus oculi Ef (a fundus oculi image Ef'), or may be a tomographic image of the fundus oculi Ef. The region of interest indicates an image region that represents an attention site in the fundus oculi Ef.

The attention site in the fundus oculi Ef includes the optic papilla, the macula, a lesion site, and so on. In the case of acquisition of images of sites other than the fundus oculi, there are regions of interest for the respective sites. The image extracting part 231 is an example of the "extracting part" and the "designating part" according to the present invention.

A specific example of a process of extracting a region of interest will be described below. First, an example of extraction of a region of interest from the fundus oculi image Ef' will be described.

The image extracting part 231 can extract a region of interest by analyzing the pixel values (luminance, RGB values, or the like) of pixels forming the fundus oculi image Ef'.

For example, when extracting a region of interest corresponding to the optic papilla, it is possible to extract the region of interest by applying image processing such as threshold processing and boundary extraction processing that are known heretofore, considering a characteristic that the region of interest is brighter than the surroundings (e.g. the luminance value is larger) and a characteristic that the shape is almost circular. After extraction of the region of interest corresponding to the optic papilla, it is possible to specify a characteristic site such as the center, center of gravity or boundary of this region of interest.

When extracting a region of interest corresponding to the macula, it is possible to extract the region of interest by applying image processing as described above, considering a characteristic that the region of interest is darker than the surroundings (e.g. the luminance value is smaller) and a characteristic that the shape is almost circular. After extraction of the region of interest corresponding to the macula, it is possible to specify a characteristic site such as the center, center of gravity or boundary of this region of interest.

When extracting a region of interest corresponding to a lesion site, it is possible to extract the region of interest by image processing as described above, by previously grasping how the lesion site is depicted in the fundus oculi image Ef', namely, what characteristic pixel values and shape the lesion site has when compared with the surroundings. The grasp of the depiction of the lesion site can be acquired by, for example, analysis of fundus oculi images having been captured in the past and of clinical data.

Next, an example of extraction of a region of interest from a tomographic image of the fundus oculi Ef will be described. When a region of interest corresponds to the optic papilla or the macula, the region of interest can be extracted based on the shape of the site. For example, the optic papilla and the macula are concave to the rear of the fundus oculi Ef (in the z direction) as compared with its surrounding sites. The image extracting part 231 specifies an image region corresponding to the surface of the fundus oculi Ef, namely, the boundary between the retina and the vitreous body, by analyzing the pixel values of the tomographic image. Furthermore, the image extracting part 231 analyzes the shape of the specified image region to specify a region that is concave in the z direction, and extracts the region as the region of interest.

A case that a region of interest is a lesion site will be described below. Lesion sites in tomographic images include those identifiable from the shape such as retinal detachment and those hard to identify from the shape such as tumors. The identifiable lesion sites can be extracted as in the case of the optic papilla or the like.

On the other hand, the lesion sites hard to identify may be represented by pixel values (such as luminance) different from their surrounding sites. In this case, the image extracting part 231 can refer to the pixel value of the tomographic image to specify an image region corresponding to the lesion site and extract the region as a region of interest.

When a region of interest (e.g., a lesion site) exists at a predetermined distance from the optic papilla or the macula, the image extracting part 231 first extracts an image position corresponding to the optic papilla or the like as described above and then specifies an image region at a predetermined distance from the image position, thereby extracting the region of interest. A distance on an image is measured considering the imaging magnification of the image or the like.

The predetermined distance may be distance alone (scalar quantity), or may be distance and direction (vector quantity). As this predetermined distance, it is possible, for example, to read and use distances having been obtained from previously acquired images and stored. Further, the image position of the optic papilla or the like may be any position in an image region, such as the center, center of gravity or boundary of the image region of the optic papilla or the like. The type of the image position may be designated by the operator, or may be automatically designated by the image extracting part 231.

The image processor 230 operating as described above includes the microprocessor 201, the RAM 202, the ROM 203, the hard disk drive 204 (control program 204*a*), and so on.

The image forming part 220 and the image processor 230 are an example of the "image forming part" of the present invention.

(User Interface)

The user interface (UI) 240 is provided with the display 240A and a manipulation part 240B. The display 240A is formed by a display device such as a display 207. The manipulation part 240B is formed by input devices and manipulation devices such as a keyboard 205 and a mouse 206.

[Scan with Signal Light and Image Processing]

A scan with the signal light LS is performed by turning around the reflecting surfaces of the Galvano mirrors 141A and 141B of the scan unit 141 as described before. The controller 210 controls the mirror drive mechanisms 241 and 242, respectively, to turn around the reflecting surfaces of the Galvano mirrors 141A and 141B, respectively, thereby scanning the fundus oculi Ef with the signal light LS.

When the reflecting surface of the Galvano mirror 141A is turned around, a scan with the signal light LS in the horizontal direction (the x-direction in FIG. 1) is performed on the fundus oculi Ef. On the other hand, when the reflecting surface of the Galvano mirror 141B is turned around, a scan with the signal light LS in the vertical direction (the y-direction in FIG. 1) is performed on the fundus oculi Ef. Further, by turning around both the reflecting surfaces of the Galvano mirrors 141A and 141B simultaneously, it is possible to scan with the signal light LS in the composed direction of the x-direction and y-direction. That is to say, by controlling the two Galvano mirrors 141A and 141B, it is possible to scan with the signal light LS in any direction on the x-y plane.

Figure 7A:
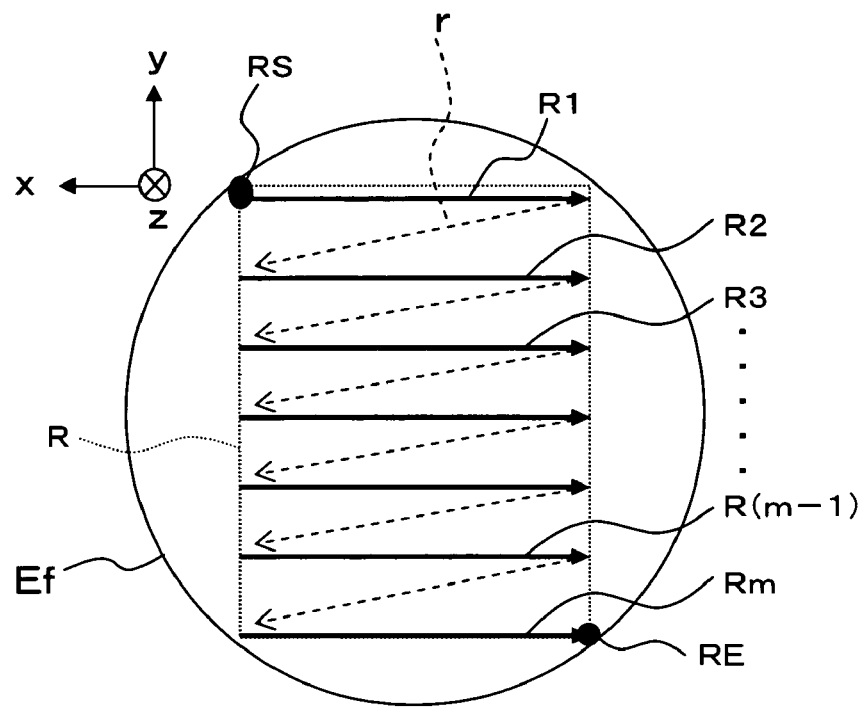
FIGS. 7A and 7B are schematic views showing an example of a scanning pattern of a signal light in the embodiment of the fundus oculi observation device functioning as the optical image measurement device according to the present invention.
Figure 7B:
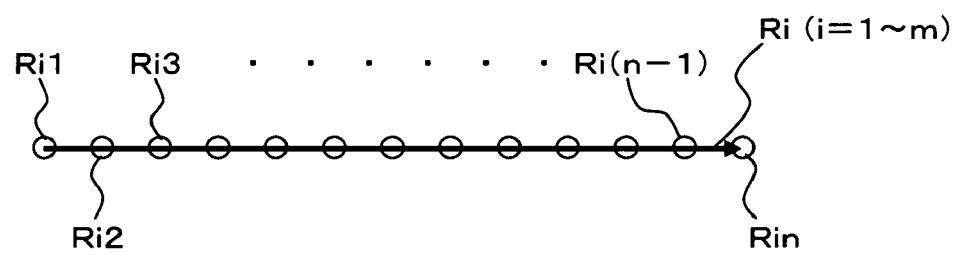

FIGS. 7A and 7B show an example of a scanning pattern of the signal light LS for forming an image of the fundus oculi Ef. FIG. 7A shows an example of the scanning pattern of the signal light LS when the fundus oculi Ef is seen from a direction in which the signal light LS enters the eye E (namely, seen from the −z side to the +z side in FIG. 1). Further, FIG. 7B shows an example of an arrangement pattern of scanning points (positions to perform image measurement) on each scanning line on the fundus oculi Ef.

As shown in FIG. 7A, a scan with the signal light LS is performed within a rectangular scanning region R set in advance.

Within the scanning region R, a plurality of (m lines of) scanning lines R1~Rm are set in the x-direction. When a scan with the signal light LS is performed along each scanning line Ri (i=1~m), a detection signal of the interference light LC is generated.

A direction of each scanning line Ri will be referred to as the "main scanning direction," and a direction orthogonal thereto will be referred to as the "sub-scanning direction." Accordingly, a scan with the signal light LS in the main scanning direction is performed by turning around the reflecting surface of the Galvano mirror 141A. A scan in the sub-scanning direction is performed by turning around the reflecting surface of the Galvano mirror 141B.

On each scanning line Ri, as shown in FIG. 7B, a plurality of (n pieces of) scanning points Ri1~Rin are set in advance.

In order to execute the scan shown in FIGS. 7A and 7B, the controller 210 firstly controls the Galvano mirrors 141A and 141B to set the entering target of the signal light LS into the fundus oculi Ef to a scan start position RS (a scanning point R11) on the first scanning line R1. Subsequently, the controller 210 controls the low-coherence light source 160 to flush the low-coherence light L0, thereby making the signal light LS enter the scan start position RS.

The CCD 184 receives the interference light LC based on the fundus oculi reflection light of the signal light LS at the scan start position RS, and outputs the detection signal to the controller 210.

Next, the controller 210 controls the Galvano mirror 141A to scan with the signal light LS in the main scanning direction and set the entering target thereof to a scanning point R12, and causes the low-coherence light L0 to flush to make the signal light LS enter a scanning point R12. The CCD 184 receives the interference light LC based on the fundus oculi reflection light of this signal light LS at the scanning point R12, and outputs the detection signal to the controller 210.

In the same way, the controller 210 makes the low-coherence light L0 flush at each scanning point while moving the entering target of the signal light LS in order of a scanning point R13, a scanning point R14, . . . a scanning point R1(n−1), and a scanning point R1n, thereby obtaining a detection signal outputted from the CCD 184 in response to the interference light LC for each scanning point.

When the measurement at the last scanning point R1n of the first scanning line R1 ends, the controller 210 controls the Galvano mirrors 141A and 141B simultaneously to move the entering target of the signal light LS to a first scanning point R21 of a second scanning line R2 along a line switching scan r. Then, by conducting the aforementioned measurement for each scanning point R2j (j=1·n) of this second scanning line R2, a detection signal corresponding to each scanning point R2j is obtained.

In the same way, the measurement is performed for each of a third scanning line R3, . . . an m−1th scanning line R(m−1) and an mth scanning line Rm, whereby a detection signal corresponding to each scanning point is acquired. Symbol RE on the scanning line Rm is a scan end position corresponding to a scanning point Rmn.

As a result, the controller 210 obtains m×n pieces of detection signals corresponding to m×n pieces of scanning points Rij (i=1~m, j=1~n) within the scanning region R. Hereinafter, a detection signal corresponding to the scanning point Rij may be represented by Dij.

Interlocking control of the movement of the scanning point and the emission of the low-coherence light L0 as described above can be implemented by synchronizing a transmission timing of a control signal to the mirror drive mechanisms 241 and 242 and a transmission timing of a control signal to the low-coherence light source 160.

As described above, when making the respective Galvano mirrors 141A and 141B operate, the controller 210 stores the position of the scanning line Ri and the position of the scanning point Rij (coordinates on the x-y coordinate system) as information representing the content of the operation. This stored content (the scan position information) is used in an image forming process as conventional.

Next, an example of image processing in the case of a scan with the signal light LS shown in FIGS. 7A and 7B will be described.

The image forming part 220 forms tomographic images of the fundus oculi Ef along each scanning line Ri (the main scanning direction). Further, the image processor 230 forms a 3-dimensional image of the fundus oculi Ef based on the tomographic images formed by the image forming part 220.

A process of forming tomographic images by the image forming part 220 includes a 2-step arithmetic process as conventional.

In the first step of the arithmetic process, based on the detection signal Dij corresponding to each scanning point Rij, an image in the depth direction (the z-direction in FIG. 1) of the fundus oculi Ef at the scanning point Rij is formed.

Figure 8:
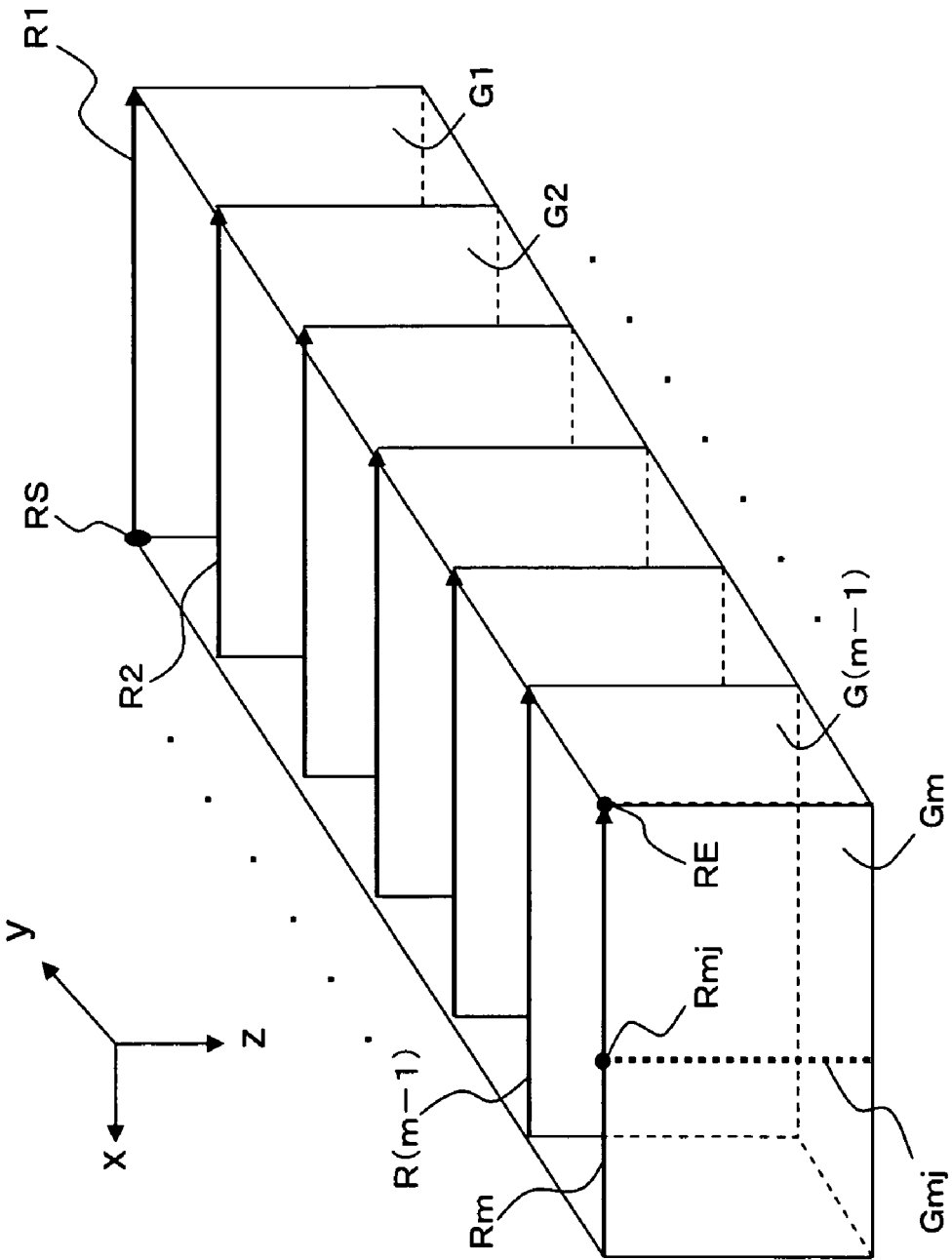
FIG. 8 is a schematic view showing an example of the scanning pattern of the signal light and a pattern of a tomographic image formed along each scanning line in the embodiment of the fundus oculi observation device functioning as the optical image measurement device according to the present invention.

FIG. 8 shows a pattern of tomographic images formed by the image forming part 220. In the second step of the arithmetic process, for each scanning line Ri, based on the images of the depth direction at the n pieces of scanning points Ri1~Rin, a tomographic image Gi of the fundus oculi Ef along the scanning line Ri is formed. At this moment, the image forming part 220 determines the arrangement and interval of the scanning points Ri1~Rin by referring to the positional information (scan position information described before) of the scanning points Ri1~Rin, and forms this scanning line Ri. Through the above process, it is possible to obtain m pieces of tomographic images G1~Gm at different positions in the sub-scanning direction (y-direction).

Next, a process of forming a 3-dimensional image of the fundus oculi Ef by the image processor 230 will be described. A 3-dimensional image of the fundus oculi Ef is formed based on the m pieces of tomographic images obtained through the abovementioned arithmetic process. The image processor 230 forms a 3-dimensional image of the fundus oculi Ef, for example, by performing a known interpolating process of interpolating an image between the adjacent tomographic images Gi and G(i+1).

In this case, the image processor 230 determines the arrangement and interval of the scanning lines Ri by referring to the positional information of the scanning lines Ri, thereby forming a 3-dimensional image. For this 3-dimensional image, 3-dimensional coordinates (x, y, z) are set, based on the positional information of each scanning point Rij (the aforementioned scan position information) and the z coordinate in an image of the depth direction.

Further, based on this 3-dimensional image, the image processor 230 can form a tomographic image of the fundus oculi Ef at a cross section in any direction other than the main scanning direction (x-direction). When the cross section is designated, the image processor 230 specifies the position of each scanning point (and/or an interpolated image of the depth direction) on this designated cross section, extracts an image of the depth direction at each of the specified positions (and/or an interpolated depth-direction image) from the 3-dimensional image, and arranges the plurality of extracted images of the depth direction, thereby forming a tomographic image of the fundus oculi Ef at the designated cross section.

An image Gmj shown in FIG. 8 represents an image in the depth direction (z-direction) at the scanning point Rmj on the scanning line Rm. In the same way, an image in the depth direction at each scanning point Rij on the scanning line Ri formed in the aforementioned first-step arithmetic process is represented as the "image Gij." The accuracy (resolution in the xy-directions) of the tomographic image Gi is high as the interval between the images Gij is small. To be specific, when the interval in the x-direction between the images Gij, namely, the interval between the images Gij on the same scanning line Ri is reduced, the accuracy in the x-direction of the tomographic image Gi increases. On the other hand, when the interval in the y-direction of the images Gij, namely, the interval between the adjacent scanning lines Ri and R(i+1) is reduced, the accuracy in the y-direction of a three-dimensional image or the like increases.

The scanning patterns of the signal light LS by the fundus oculi observation device 1 are not limited to those described above.

For example, it is possible to configure to scan with the signal light LS only in the horizontal direction (the x-direction) (a horizontal scan), scan only in the vertical direction (the y-direction) (a vertical scan), scan in the cruciform manner with one line in each of the horizontal and vertical directions (a cross scan), scan radially (a radial scan), scan circularly (a circular scan), scan concentrically (a concentric scan), and scan helically (a helical scan). The scanning pattern shown in FIG. 7 allows formation of a 3-dimensional image and will be referred to as a 3-dimensional scan. In other words, as previously described, since the scan unit 141 is configured to be capable of scanning with the signal light LS in the x-direction and y-direction independently, it is possible to scan with the signal light LS along any trajectory on the x-y plane.

The operator can select a desired scanning pattern of the signal light LS by manipulating the manipulation part 240B, for example.

Further, in the case of acquiring an image of the same site plural times as in a follow-up, it is possible to store an actually applied scanning pattern into the storage 212. The controller 211 can read the stored information to reproduce the past scanning pattern and scan with the signal light LS.

Figure 9:
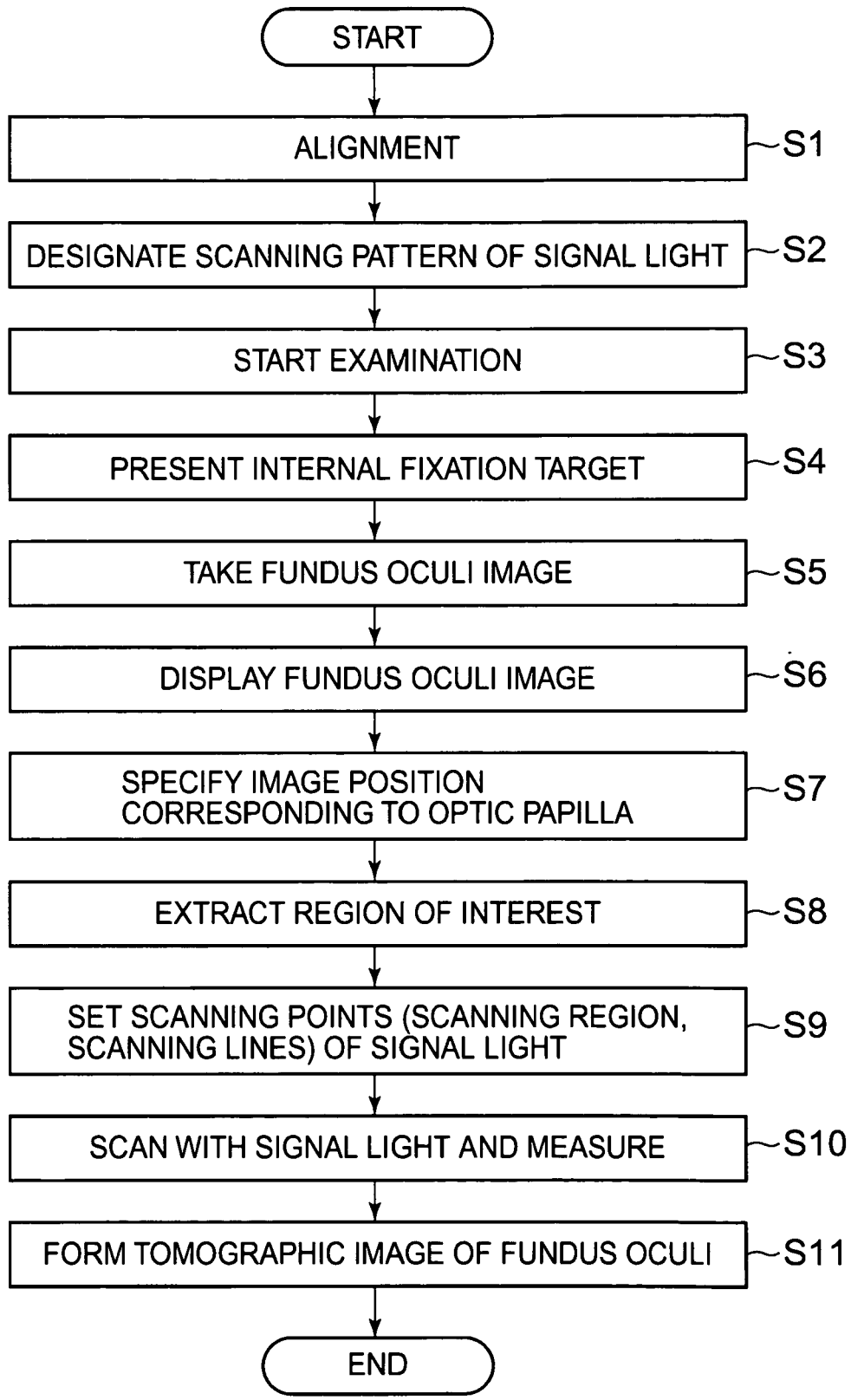
FIG. 9 is a flowchart showing an example of a usage pattern of the embodiment of the fundus oculi observation device functioning as the optical image measurement device according to the present invention.

[Usage Pattern]
A usage pattern of the fundus oculi observation device 1 will be described.
[First Usage Pattern]
Referring to a flow chart of FIG. 9, a first usage pattern of the fundus oculi observation device 1 will be described. The first usage pattern is to automatically extract a region of interest from an image of the fundus oculi Ef, and scan with the signal light LS while changing a scan interval based on the result of the extraction.

First, the eye E is placed at a predetermined measurement position (a position facing the objective lens 113), and alignment between the eye E and the device is executed (S1). The operator designates a scanning pattern of the signal light LS on the fundus oculi Ef (S2), and manipulates the manipulation part 240B to request start of the examination (S3). In this case, the scanning pattern designated in step 2 includes the cross scan, the concentric scan, and the 3-dimensional scan.

The main controller 211 controls the LCD 140 to present an internal fixation target on the eye E (S4). In this case, a fixation target for fixing the eye E is presented at a fixation position for acquiring an image of the optic papilla. The fixation position of the eye E is designated in advance by, for example, the operator. Also in the case of fixation at a fixation position for acquiring an image of the macula or the center of the fundus oculi, the following process is similarly executed. Besides, the operator can appropriately adjust the presented position of the internal fixation target by the LCD 140, namely, the fixation position of the eye E, by manipulating the manipulation part 240B.

The main controller 211 controls the observation light source 101 and the imaging device 12 (or the imaging light source 103 and the imaging device 10) to capture the fundus oculi image Ef' of the fundus oculi Ef (S5), and controls the display 240A to display this fundus oculi image Ef' (S6). The displayed image may be either a motion image or a still image.

The image extracting part 231 analyzes the captured fundus oculi image Ef' and specifies an image position corresponding to the optic papilla (e.g. central papilla) (S7), and then extracts an image region (a region of interest) at a predetermined distance from the image position (S8). The position of this region of interest is obtained as coordinate values of the aforementioned x-y coordinate system.

The region of interest is arbitrarily determined based on a position (an attention position) at a predetermined distance from the aforementioned image position. For example, a region having a predetermined shape (a circular shape, oval shape, rectangular shape, or the like) about the attention position can be assumed as a region of interest. Besides, it is possible to configure so that, when the attention position is specified, this attention position is displayed and the operator sets a region of interest by using the manipulation part 240B.

Further, when the region of interest has a characteristic shape like the macula or the optic papilla, it is possible to extract the region of interest with the characteristic shape as the aforementioned predetermined shape. Further, for example, when the region of interest has a distinct shape like a lesion site, it is possible to extract the region of interest as the aforementioned predetermined shape by reading out shape information from stored shapes in images obtained in the past.

The scan setting part 213 sets scanning points (a scanning region, scanning lines) of the signal light LS on the fundus oculi Ef based on the scanning pattern designated in step 2 and the coordinate values of the region of interest extracted in step 8 (S9). In this case, the scan setting part 213 sets the scanning region of the signal light LS so as to include the region of interest and also sets the scanning points so that a scan interval on an attention site in the fundus oculi Ef corresponding to the region of interest is smaller than a scan interval on other regions. The positions of the scanning points having been set are stored in the storage 212 as the aforementioned scanning position information.

Figure 10:
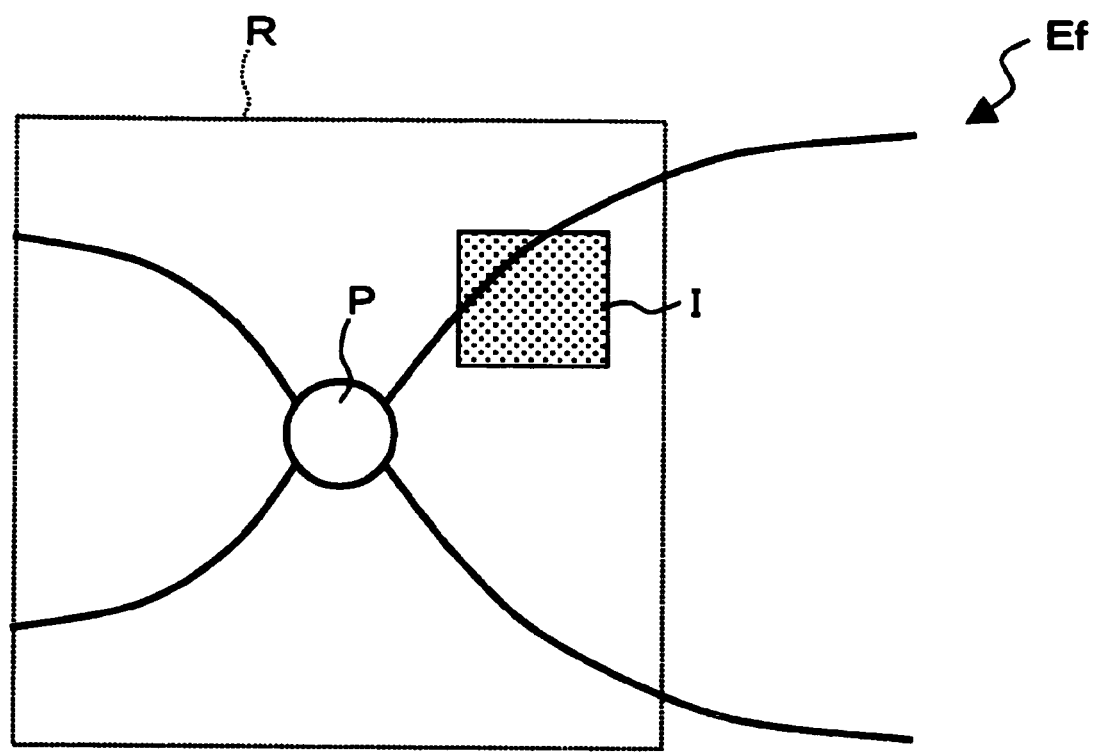
FIG. 10 is a schematic explanation diagram showing an example of a scanning pattern of the signal light in the usage pattern of the embodiment of the fundus oculi observation device functioning as the optical image measurement device according to the present invention.

FIG. 10 shows an example of a setting pattern of a scanning region of the signal light LS on the fundus oculi Ef in the case of executing a 3-dimensional scan. Reference symbol P represents the optic papilla of the fundus oculi Ef. Reference symbol I represents an attention site in the fundus oculi Ef corresponding to the region of interest. The scanning region R of the signal light LS is set so as to include the attention site I. Within the scanning region R, scanning lines R1~Rm are set as shown in FIG. 7.

The coordinate values of each position within the attention site I correspond to the coordinate values of the aforementioned region of interest. When the scanning region R and the number (m) of the scanning lines are determined, the coordinate values of each position on each scanning line Ri are also determined. The scan setting part 213 sets the scanning points at an interval d1 on the attention site I and sets the scanning points at an interval d2 (>d1) on sites other than the attention site I, based on the coordinate values of the attention site I and the coordinate values of each scanning line Ri.

Thus, it is possible to set the scan interval on the attention site I corresponding to the region of interest so as to be smaller than the scan interval on other regions.

The interval of scanning lines can also be changed depending on an attention site. For example, when setting the scanning line Ri, it is possible to set scanning lines passing through the attention site I at an interval D1 and set other scanning lines at an interval D2(>D1).

Besides, it is possible to combine this setting of the interval of scanning lines and the aforementioned setting of the interval of scanning points.

Thus, the "scan interval" indicates at least either the interval of scanning points on one scanning line or the interval of scanning lines. Also in scanning patterns other than the 3-dimensional scan, it is possible to set the scan interval in a similar manner.

The main controller 211 controls the mirror drive mechanisms 241 and 242 based on the scanning position information obtained in step 9 to sequentially emit the signal light LS to the scanning points having been set (S10). The signal light LS emitted to each of the scanning points is superimposed on the reference light LR, and the interference light LC is thereby generated. Then, the interference light LC corresponding to each of the scanning points is divided into spectra and detected by the spectrometer 180.

The image forming part 220 forms a tomographic image of the fundus oculi Ef based on a detection signal outputted from the CCD 184 of the spectrometer 180 (S11). In this process, the scanning position information is also referred to. The image processor 230 forms a 3-dimensional image of the fundus oculi Ef as needed based on the tomographic image formed in step 11 and the scanning position information.

Since an attention site in the fundus oculi Ef is scanned with the signal light LS at a relatively small scan interval in the first usage pattern, the tomographic image formed in step 11 depicts the attention site in the fundus oculi Ef with high accuracy (high resolution). On the other hand, since a site other than the attention site is scanned with the signal light LS at a relatively large scan interval, a time for measurement of the tomographic image is relatively short. Therefore, according to the first usage pattern, it is possible to quickly acquire a highly accurate image of an attention site in the fundus oculi Ef.

For example, the first usage pattern is suitable for a thickness measurement of the retinal pigment epithelium, the optic nerve fiber layer or the like, and for an observation of a lesion site such as retinal detachment and tumor.

In the thickness measurement of a layer such as the retina, the thickness is often measured in a site (an attention site) at a predetermined distance from the central papilla, the fovea centralis, or the like. Therefore, by applying the first usage pattern, it is possible to quickly and easily acquire a highly accurate image of the attention site. As a result, it is possible to increase the accuracy in thickness measurement and also possible to shorten the examination time.

Besides, the position of a lesion site is often specified based on the distance (and direction) from the central papilla or the fovea centralis. Therefore, by applying the first usage pattern, it is possible to quickly and easily acquire a highly accurate image of the lesion site. As a result, it is possible to closely observe the lesion site and also possible to shorten the examination time.

[Second Usage Pattern]

Figure 11:
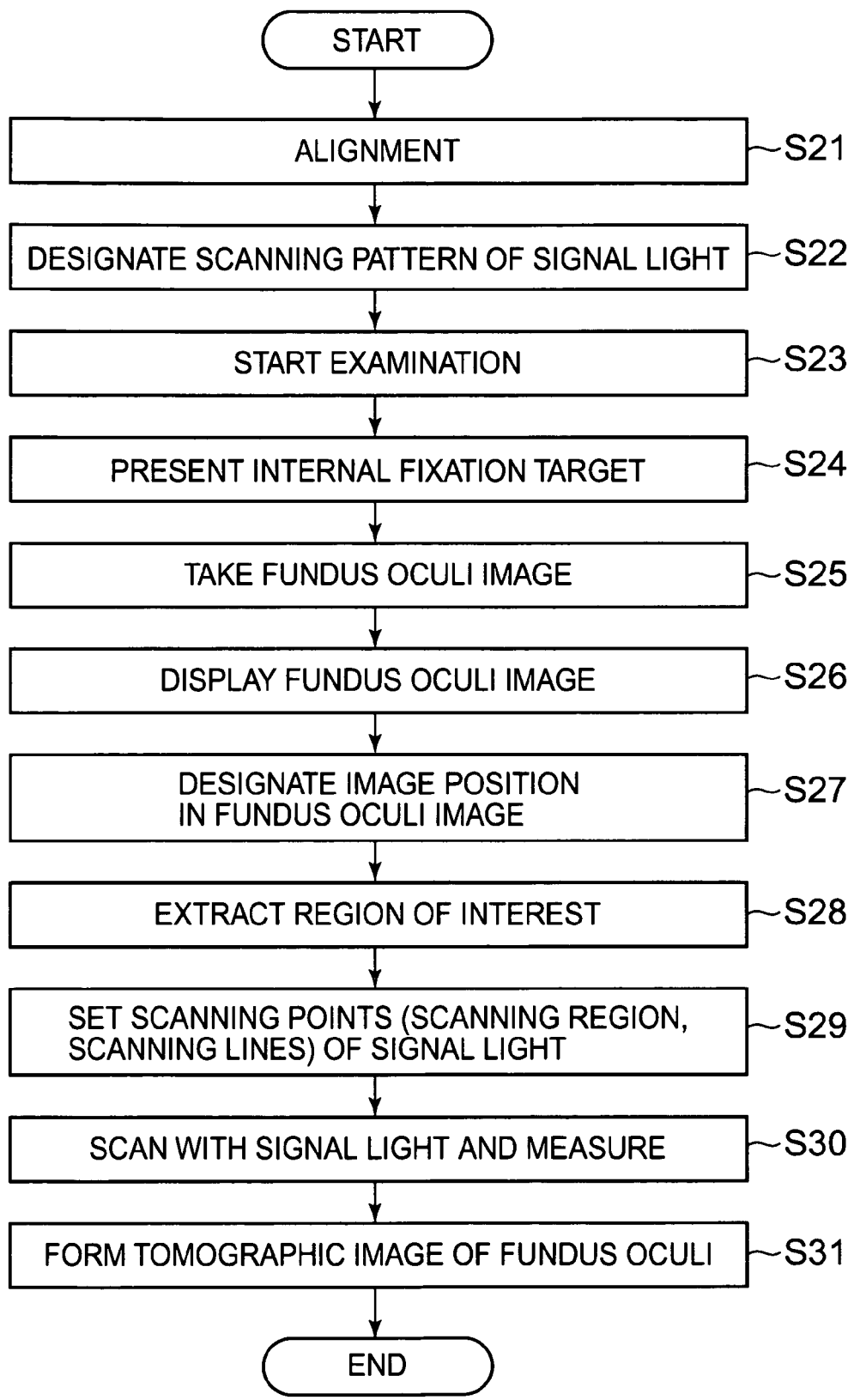
FIG. 11 is a flowchart showing an example of a usage pattern of the embodiment of the fundus oculi observation device functioning as the optical image measurement device according to the present invention.

With reference to a flow chart of FIG. 11, a second usage pattern of the fundus oculi observation device 1 will be described. In the second usage pattern, the fundus oculi observation device 1 extracts a region of interest based on a position designated by the operator in an image of the fundus oculi Ef, and scans with the signal light LS while changing the scan interval based on the result of the extraction.

First, after alignment is performed (S21), a scanning pattern of the signal light LS is designated (S22) and start of an examination is requested (S23) as in the first usage pattern, the fundus oculi observation device 1 presents an internal fixation target on the eye E (S24), captures the fundus oculi image Ef' of the fundus oculi Ef (S25) and displays this fundus oculi image Ef' (S26).

The operator manipulates the manipulation part 240B and designates a desired position in the displayed fundus oculi image Ef' (S27). In the case of acquisition of an OCT image of the optic papilla, an image position corresponding to, for example, the central papilla is designated. On the other hand, in the case of acquisition of an OCT image of the macula, an image position corresponding to, for example, the fovea centralis is designated. It is possible to perform this designation of the image position by, for example, clicking the mouse 206.

The image extracting part 231 extracts an image region (a region of interest) at a predetermined distance from the image position designated in the fundus oculi image Ef' (S28). This process is executed as in the first usage pattern.

The scan setting part 213 sets scanning points (scanning region, scanning lines) of the signal light LS on the fundus oculi Ef, based on the scanning pattern designated in step 22 and the coordinate values of the region of interest extracted in step 28 (S29). In this case, as in the first usage pattern, the scanning region of the signal light LS is set so as to include the region of interest, and the scanning points are set so that the scan interval for an attention site in the fundus oculi Ef corresponding to the region of interest is smaller than the scan interval for other regions. The positions of the scanning points having been set are stored as scanning position information.

The main controller 211 controls to scan with the signal light LS based on the scanning position information obtained in step 29 (S30). Thus, the spectral distribution of the interference light LC corresponding to each of the scanning points is detected by the spectrometer 180.

The image forming part 220 forms a tomographic image of the fundus oculi Ef based on a detection signal from the CCD 184 (S31).

Besides, the image processor 230 forms a 3-dimensional image of the fundus oculi Ef as needed.

According to the second usage pattern, as in the first usage pattern, it is possible to quickly acquire a highly accurate image of an attention site in the fundus oculi Ef. Moreover, according to the second usage pattern, the operator can designate a desired image position, and a region of interest corresponding to the image position is automatically extracted. Therefore, it is possible to easily execute a measurement that satisfies the demand of the operator.

Although the operator designates an image position in the fundus oculi image Ef' in the aforementioned second usage pattern, the operator may designate an image position in a tomographic image of the fundus oculi Ef. In this case, for example, the fundus oculi observation device 1 is configured to operate so as to acquire a tomographic image in step 25 and display this tomographic image in step 26.

As well as the first usage pattern, the second usage pattern is suitable for a measurement of the layer thickness of the retina and an observation of a lesion site.

[Third Usage Pattern]

Figure 12:
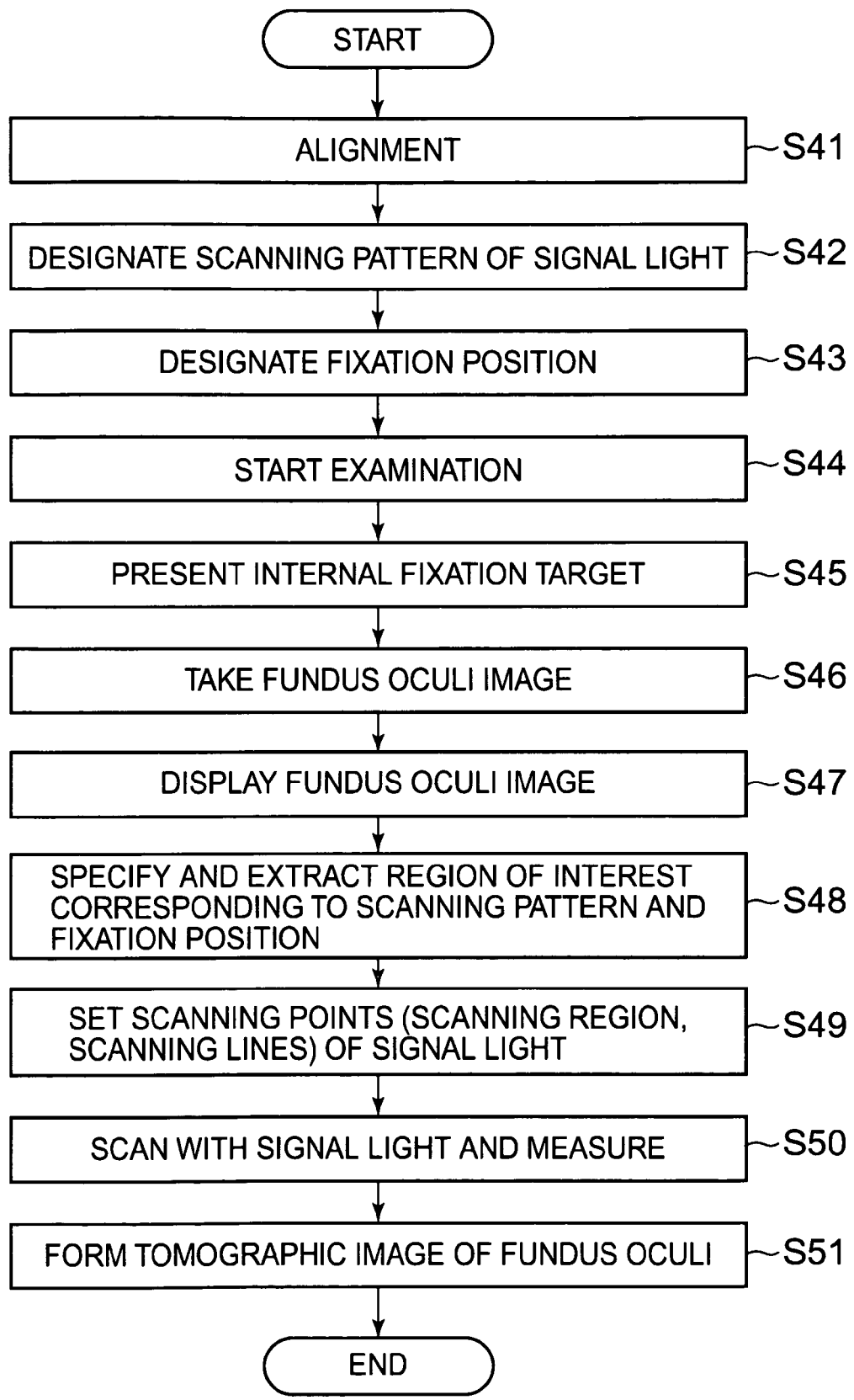
FIG. 12 is a flowchart showing an example of a usage pattern of the embodiment of the fundus oculi observation device functioning as the optical image measurement device according to the present invention.

With reference to a flow chart of FIG. 12, a third usage pattern of the fundus oculi observation device 1 will be described. In the third usage pattern, the fundus oculi observation device 1 specifies and extracts a region of interest based on a fixation position and a scanning pattern, and scans with the signal light LS while changing a scan interval based on the result of the extraction.

First, alignment is performed (S41) and a scanning pattern of the signal light LS is designated (S22) as in the first usage pattern.

Next, the operator manipulates the manipulation part 240B to designate a fixation position of the eye E (S43). When start of the examination is requested (S44), the fundus oculi observation device 1 presents an internal fixation target on the eye E (S45), captures the fundus oculi image Ef' of the fundus oculi Ef (S46), and displays this fundus oculi image Ef' (S47).

The image extracting part 231 specifies and extracts a region of interest in the fundus oculi image Ef' based on the scanning pattern designated in step 42 and the fixation position designated in step 43 (S48).

A process of specifying a region of interest will be described below. When the fixation position and the scanning pattern are determined, a site to be examined, the purpose of the examination, and so on may be automatically determined. For example, an OCT image acquired when the fixation position for the optic papilla is set and the circular scan or concentric scan is set is usually provided for a thickness measurement of the optic nerve fiber layer or the like for diagnosis of glaucoma. An OCT image acquired when the fixation position for the optic papilla is set and the cross scan is set, is usually provided for a measurement of the C/D ratio or R/D ratio for diagnosis of glaucoma. An OCT image acquired when the fixation position for the macula is set and the 3-dimensional scan or radial scan is set is provided for a thickness measurement of the retinal pigment epithelium or an observation of a lesion site such as retinal detachment.

Accordingly, correspondence information (table information or the like) in which the correspondence relationships as described above are recorded is previously generated and stored in the storage 212. The image extracting part 231 refers to this correspondence information, specifies an attention site corresponding to the designated scanning pattern and fixation position, and specifies a region of interest in the fundus oculi image Ef' corresponding to this attention site. When, as in the case of a lesion site, an attention site exists away from a characteristic site (the central papilla, the fovea centralis or the like) in the fundus oculi Ef, it is possible to specify a region of interest by a similar method to that in the first usage pattern.

Moreover, in a case that two or more regions of interest correspond to a certain combination of the fixation position and the scanning pattern, it is possible to present these two or more regions of interest in a selectable manner. For example, by displaying a pull-down menu, a dialog box or the like on the display 240A, it is possible to present two or more regions of interest in a selectable manner.

The scan setting part 213 sets scanning points (a scanning region, scanning lines) of the signal light LS on the fundus oculi Ef based on the scanning pattern designated in step 42 and the coordinate values of the region of interest extracted in step 48 (S49).

In this process, as in the first usage pattern, a scanning region of the signal light LS is set so as to include the region of interest, and scanning points are set so that a scan interval on an attention site in the fundus oculi Ef corresponding to the region of interest is smaller than a scan interval on other regions. The positions of the scanning points having been set are stored as scanning position information.

The main controller 211 controls to scan with the signal light LS based on the scanning position information obtained in step 49 (S50). Consequently, the spectral distribution of the interference light LC corresponding to each of the scanning points is detected by the spectrometer 180.

The image forming part 220 forms a tomographic image of the fundus oculi Ef based on a detection signal from the CCD 184 (S51).

Besides, the image processor 230 forms a 3-dimensional image of the fundus oculi Ef as needed.

According to the third usage pattern, as in the first usage pattern, it is possible to quickly acquire a highly accurate image of an attention site in the fundus oculi Ef. Moreover, according to the third usage pattern, only by designating the scanning pattern of the signal light LS and the fixation position of the eye E, a region of interest corresponding to the designated matters is automatically extracted, so that it is possible to facilitate the measurement operation.

[Fourth Usage Pattern]

With reference to a flow chart of FIG. 13, a fourth usage pattern of the fundus oculi observation device 1 will be described. In the fourth usage pattern, the fundus oculi observation device 1 extracts a region of interest having been manually designated by the operator, scans with the signal light LS while changing a scan interval based on the result of the extraction.

First, when alignment is performed (S61), a scanning pattern of the signal light LS is designated (S62), and start of the examination is requested (S63) as in the first usage pattern, the fundus oculi observation device 1 presents an internal fixation target on the eye E (S64), captures the fundus oculi image Ef' of the fundus oculi Ef (S65), and displays this fundus oculi image Ef' (S66).

The operator manipulates the manipulation part 240B and designates a desired image region in the displayed fundus oculi image Ef' as a region of interest (S67). It is possible to perform the designation of the region of interest by dragging the mouse 206, for example.

The image extracting part 231 extracts the region of interest designated in the fundus oculi image Ef' (S68).

The scan setting part 213 sets scanning points (a scanning region, scanning lines) of the signal light LS on the fundus oculi Ef, based on the scanning pattern designated in step 62 and the coordinate values of the region of interest extracted in step 68 (S69).

In this process, as in the first usage pattern, the scanning region of the signal light LS is set so as to include the region of interest, and the scanning points are set so that the scan interval on an attention site in the fundus oculi Ef corresponding to the region of interest is smaller than the scan interval on other regions. The positions of the scanning points having been set are stored as scanning position information.

The main controller 211 controls to scan with the signal light LS based on the scanning position information obtained in step 69 (S70). Consequently, the spectral distribution of the interference light LC corresponding to each of the scanning points is detected by the spectrometer 180.

The image forming part 220 forms a tomographic image of the fundus oculi Ef based on a detection signal from the CCD 184 (S71).

Moreover, the image processor 230 forms a 3-dimensional image of the fundus oculi Ef as needed.

According to the fourth usage pattern, as in the first usage pattern, it is possible to quickly acquire a highly accurate image of an attention site in the fundus oculi Ef. Moreover, according to the fourth usage pattern, the operator can designate a desired region of interest, and the region of interest is automatically extracted, so that it is possible to easily execute a measurement that satisfies the demand of the operator.

Instead of designation of a region of interest in the fundus oculi image Ef', the region of interest may be designated in a tomographic image of the fundus oculi Ef. In this case, for example, the fundus oculi observation device 1 may be configured to operate so as to acquire a tomographic image in step 65 and display this tomographic image in step 66.

Besides, in step 65, it is possible to acquire a tomographic image, analyze this tomographic image, and measure the thickness of various layers. Further, it is possible to compare this layer thickness with a predetermined acceptable range, determine that there may be abnormality (such as a lesion site) when the thickness is out of the acceptable range, and set the measurement region of this layer to the region of interest. These processes are performed by the image processor 230 and the controller 210, for example. By performing such processes, it is possible to automatically set an abnormal site in the fundus oculi Ef as a region of interest.

The aforementioned acceptable range can be determined based on clinical data obtained by, for example, measuring the thickness of the layer of a normal eye in advance. This acceptable range is prestored in the storage 212, for example.

Further, patient identification information such as a patient ID and positional information of a region of interest can be associated and stored into the storage 212. In the next (or later) examination, when patient identification information is inputted into the arithmetic and control unit 200, the main controller 211 can acquire positional information of the region of interest associated with the patient identification information from the storage 212 and set the region of interest based on the positional information. Since it is possible to automatically set the region of interest of the past examination by executing the above process, it is possible to easily and quickly observe a change with time in the attention site.

The positional information of the region of interest can be generated as displacement of the region of interest with respect to a characteristic point (such as the central papilla, the fovea centralis or the vascular bifurcation) in the fundus oculi Ef. Moreover, the fixation position (a projection position (a display position) of the internal fixation target) and the position of the region of interest in the image acquired at this fixation position may be defined as the positional information. Thus, the positional information includes arbitrary information that allows specification of the position of the region of interest.

[Action and Effect]

The actions and effects of the fundus oculi observation device 1 as described above will be described below.

The fundus oculi observation device 1 functions as an optical image measurement device that divides the low-coherence light L0 into the signal light LS and the reference light LR, superimposes the signal light LS propagated through the fundus oculi Ef and the reference light LR propagated through the reference mirror 174 to generate and detect the interference light LC, and forms an OCT image (a tomographic image or a 3-dimensional image) of the fundus oculi Ef based on the result of the detection.

Further, the fundus oculi observation device 1 is provided with a scan unit 141 that scans the fundus oculi Ef with the signal light LS, and a controller 210 that controls the scan unit 141 to scan with the signal light LS while changing a scan interval when performing a series of scans of the signal light LS.

The "series of scans with the signal light" indicates a scan with the signal light executed in a series of processes for acquiring one or more tomographic images, such as the aforementioned examples of the scanning pattern (horizontal scan, vertical scan, cross scan, radial scan, circular scan, concentric scan, helical scan, and 3-dimensional scan).

According to the fundus oculi observation device 1, in the series of scans with the signal light LS, it is possible to scan with the signal light LS while changing a scan interval for every site in the fundus oculi Ef.

For example, as in the first through fourth usage patterns described above, it is possible to set a scan interval on an attention site in the fundus oculi Ef so as to be smaller and set a scan interval on other sites so as to be larger. The size of the scan interval mentioned above is a relative one on the attention site and the other sites.

Consequently, it is possible to acquire a highly accurate image on an attention site and shorten a time taken for scanning other sites.

Therefore, according to the fundus oculi observation device 1, it is possible to quickly acquire a highly accurate image of an attention site in the fundus oculi Ef.

Further, according to the fundus oculi observation device 1, it is possible to store information representing a scan interval of the signal light LS in a series of scans into the storage 212 and newly execute a series of scans based on the information. Therefore, it is possible to easily reproduce scans similar to the series of scans executed in the past. Consequently, it is possible to increase convenience in the case of acquiring images of the same attention site in the fundus oculi Ef plural times, for example, in a follow-up.

Further, according to the fundus oculi observation device 1, it is possible to store information representing a scan interval of the signal light LS in a series of scans and form a 3-dimensional image of the fundus oculi Ef based on the information. Therefore, it is possible to quickly acquire a 3-dimensional image that depicts an attention site with high accuracy.

[Modification]

The configuration described above is merely an example for favorably implementing the present invention. Therefore, it is possible to properly make any modification within the scope and intent of the present invention.

In the aforementioned embodiments, a scan with the signal light LS is executed by changing a scan interval on an attention site in the fundus oculi Ef and a scan interval on other sites. However, the changing pattern of the scan intervals is not limited to this pattern.

For example, when an attention site in the fundus oculi Ef has a complicated shape, change of the scanning points of the signal light LS may be complicated. In this case, it is possible to configure so as to set a partial region in the fundus oculi Ef including an attention site (it is desired that the partial region has a simpler shape than the attention site) and change a scan interval in this partial region and a scan interval in other regions.

Further, the aforementioned embodiment describes a case of one attention site. In a case that there are two or more attention sites, as in the aforementioned embodiment, it is possible to change so that the scan intervals in these attention sites are smaller and the scan intervals in other sites are larger. The scan intervals in each of the attention sites may be all the same, or may be different from each other.

In the aforementioned embodiment, the position of the reference mirror 174 is changed and the difference in light path length between the light paths of the signal light LS and the reference light LR is thereby changed. However, the method for changing the difference in light paths is not limited to this. For example, by integrally moving the retinal camera unit 1A and the OCT unit 150 with respect to the eye E to change the light path length of the signal light LS, it is possible to change the difference in light path length. It is also possible to change the difference in light path length, by moving the eye E in the depth direction (z-direction).

Although the fundus oculi observation device described in the aforementioned embodiments includes a Fourier-domain type of optical image measurement device, it is possible to apply the configuration of the present invention to any optical image measurement device of a system that scans the eye with light, such as the Swept Source type.

Further, although a device that acquires an OCT image of the fundus oculi is described in the aforementioned embodiments, the configuration of the aforementioned embodiments can also be applied to a device capable of acquiring an OCT image of other sites in the eye, such as the cornea. Also, the present invention can be applied to an optical image measurement device that measures OCT images of various types of measurement objects other than eyes. For example, the optical image measurement device according to the present invention can be applied to any field such as the fields of engineering and biology.

[Program]

A program for controlling the device according to the present invention will be described. The control program 204a in the above embodiment is an example of the program of the present invention.

The program according to the present invention is for controlling an optical image measurement device of a type that scans a measurement object with light. This optical image measurement device is provided with a computer, as well as the aforementioned interference-light generator, detector, and scanner. In the aforementioned embodiment, the arithmetic and control unit 200 functions as the computer.

This program is characterized by, when performing a series of scans with a signal light, making the computer function as a controller that controls the scanner to scan with the signal light while changing a scan interval.

According to the program, in a series of scans with a signal light, it is possible to scan with the signal light while changing a scan interval for every site in a measurement object. Consequently, it is possible to acquire a highly accurate image by scanning an attention site in the measurement object with the signal light at a smaller scan interval, whereas it is possible to scan other sites with the signal light at a larger scan interval and reduce a scanning time.

Therefore, according to this program, it is possible to quickly acquire a highly accurate image of an attention site in a measurement object.

The program according to the present invention can be stored in any storage medium that can be read by a drive device of the computer. For example, it is possible to use a storage medium such as an optical disk, a magneto-optical disk (CD-ROM, DVD-RAM, DVD-ROM, MO or the like), or a magnetic storage medium (hard disk, Floppy™ disk, ZIP or the like). It is also possible to store into a storage device such as a hard disk drive or a memory. Besides, it is also possible to transmit this program via a network such as the Internet or LAN.

The invention claimed is:

1. An optical image measurement device that has: an interference-light generator configured to split a low-coherence light into a signal light and a reference light and superimpose the signal light propagated through a measurement object and the reference light propagated through a reference object to generate an interference light; a detector configured to detect the generated interference light; and an image forming part configured to form an image of the measurement object based on a detection result from the detector, the optical image measurement device comprising:
    a scanner configured to scan the measurement object with the signal light; and
    a controller configured to control the scanner to scan with the signal light in different scan intervals for different regions, in execution of a series of scans with the signal light, wherein
    the scan interval is an interval between a scanned point and a next point for scanning, or an interval between a scan line and a next scan line, which are scanned in parallel.

2. The optical image measurement device according to claim 1, further comprising a designating part configured to designate a region of interest in the image of the measurement object, wherein the controller is configured to control to scan with the signal light in a scan interval, a partial region of the measurement object including an attention site corresponding to the designated region of interest, while to scan in a smaller scan interval than the scan interval of a region other than the partial region.

3. The optical image measurement device according to claim 2, wherein the designating part includes an extracting part configured to analyze the image of the measurement object and extracts the region of interest.

4. The optical image measurement device according to claim 3, wherein:
    the measurement object is a fundus oculi; and
    the extracting part is configured to extract an image region at a predetermined distance from an image position corresponding to an optic papilla of the fundus oculi as the region of interest.

5. The optical image measurement device according to claim 3, wherein:
    the measurement object is a fundus oculi; and
    the extracting part is configured to extract an image region at a predetermined distance from an image position corresponding to a macula of the fundus oculi as the region of interest.

6. The optical image measurement device according to claim 4, wherein the extracting part is configured to analyze an image of the fundus oculi to specify the image position, and extract an image region at the predetermined distance from the specified image position as the region of interest.

7. The optical image measurement device according to claim 5, wherein the extracting part is configured to analyze an image of the fundus oculi to specify the image position, and extract an image region at the predetermined distance from the specified image position as the region of interest.

8. The optical image measurement device according to claim 4, wherein:
the designating part includes a manipulation part for designating the image position in an image of the fundus oculi; and
the extracting part is configured to extract an image region at the predetermined distance from the designated image position as the region of interest.

9. The optical image measurement device according to claim 5, wherein:
the designating part includes a manipulation part for designating the image position in an image of the fundus oculi; and
the extracting part is configured to extract an image region at the predetermined distance from the designated image position as the region of interest.

10. The optical image measurement device according to claim 6, wherein the designating part includes an imaging part configured to capture a 2-dimensional image of a surface of the fundus oculi as the image of the fundus oculi.

11. The optical image measurement device according to claim 7, wherein the designating part includes an imaging part configured to capture a 2-dimensional image of a surface of the fundus oculi as the image of the fundus oculi.

12. The optical image measurement device according to claim 8, wherein the designating part includes an imaging part configured to capture a 2-dimensional image of a surface of the fundus oculi as the image of the fundus oculi.

13. The optical image measurement device according to claim 9, wherein the designating part includes an imaging part configure to capture a 2-dimensional image of a surface of the fundus oculi as the image of the fundus oculi.

14. The optical image measurement device according to claim 2, wherein:
the measurement object is an eye;
the optical image measurement device further comprises:
a projecting part configured to project a fixation target for fixing at one of two or more fixation positions, onto the eye; and
a scan designating part for designating a scanning pattern of the signal light on the eye; and
the designating part is configured to designate the region of interest based on the fixation position by the projecting part and the designated scanning pattern.

15. The optical image measurement device according to claim 2, wherein the designating part includes a manipulation part for designating the region of interest.

16. The optical image measurement device according to claim 15, wherein:
the designating part includes an imaging part configured to capture a 2-dimensional image of a surface of the fundus oculi as the image of the measurement object, and a display configured to display the captured 2-dimensional image; and
the manipulation part is used for designating the region of interest in the displayed 2-dimensional image.

17. The optical image measurement device according to claim 1, wherein the controller includes a storage configured to store information representing the scan interval of the signal light in the series of scans, and configured to control to scan with the signal light based on the stored information, in execution of a new series of scans with the signal light.

18. The optical image measurement device according to claim 1, wherein:
the controller includes a storage configured to store information representing the scan interval of the signal light in the series of scans; and
the image forming part is configured to form a 3-dimensional image of the measurement object based on the stored information.

19. A computer implementable program stored on a non-transitory computer readable medium configured to control an optical image measurement device that has:
an interference-light generator configured to split a low-coherence light into a signal light and a reference light and superimpose the signal light propagated through a measurement object and the reference light propagated through a reference object to generate an interference light;
a detector configured to detect the generated interference light;
a scanner configured to scan the measurement object with the signal light; and
a computer, and that forms an image of the measurement object based on a detection result from the detector,
wherein the program makes the computer function as a controller configured to control the scanner to scan with the signal light in different scan intervals for different regions, in execution of a series of scans with the signal light, and
wherein the scan interval is an interval between a scanned point and the next point for scanning, or an interval between a scan line and a next scan line, which are scanned in parallel.

* * * * *